(12) United States Patent
Cole et al.

(10) Patent No.: US 11,317,802 B2
(45) Date of Patent: May 3, 2022

(54) SYSTEMS, DEVICES, AND METHODS FOR INTEGRATION OF AN ANALYTE DATA READER AND MEDICATION DELIVERY DEVICE

(71) Applicant: ABBOTT DIABETES CARE INC., Alameda, CA (US)

(72) Inventors: Jean-Pierre Cole, Tracy, CA (US); Cherie A. Bulala, Berkeley, CA (US); Theodore J. Kunich, Pleasanton, CA (US); Xuandong Hua, Mountain View, CA (US); Hila F. Ralston, Alameda, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 0 days.

(21) Appl. No.: 16/518,691

(22) Filed: Jul. 22, 2019

(65) Prior Publication Data

US 2019/0343385 A1 Nov. 14, 2019

Related U.S. Application Data

(63) Continuation of application No. PCT/US2018/018232, filed on Feb. 14, 2018.

(60) Provisional application No. 62/459,441, filed on Feb. 15, 2017.

(51) Int. Cl.
*A61B 5/00* (2006.01)
*H04W 4/80* (2018.01)
*A61B 5/145* (2006.01)
*A61M 5/14* (2006.01)
*H01M 10/0525* (2010.01)

(52) U.S. Cl.
CPC .......... *A61B 5/002* (2013.01); *A61B 5/14532* (2013.01); *A61M 5/14* (2013.01); *H01M 10/0525* (2013.01); *H04W 4/80* (2018.02); *A61M 2205/3584* (2013.01)

(58) Field of Classification Search
CPC ....... H04W 4/80; A61B 5/14532; A61M 5/14; H01M 10/0525
See application file for complete search history.

(56) References Cited

U.S. PATENT DOCUMENTS

| 2002/0096543 | A1  | 7/2002 | Juselius |  |
|---|---|---|---|---|
| 2011/0213225 | A1  | 9/2011 | Bernstein et al. |  |
| 2012/0040611 | A1* | 2/2012 | Griffin | H04W 52/028 |
|  |  |  |  | 455/41.1 |
| 2012/0231734 | A1* | 9/2012 | Symons | H04B 5/0075 |
|  |  |  |  | 455/41.1 |
| 2012/0238852 | A1* | 9/2012 | Brauker | A61M 11/00 |
|  |  |  |  | 600/365 |

(Continued)

OTHER PUBLICATIONS

WO, PCT/US18/18232 ISR and Written Opinion, dated May 24, 2018.

*Primary Examiner* — Wen W Huang
(74) *Attorney, Agent, or Firm* — One LLP

(57) ABSTRACT

Systems, devices and methods are provided for the integration of an analyte data reader and a medication delivery device. The integrated device can include a medication delivery portion, wireless communications circuitry configured to receive data indicative of an analyte level, and electronics. The integrated device can also include one or more near-field communication (NFC) antennas. Example embodiments of adverse condition protection features of the integrated device are also provided.

18 Claims, 19 Drawing Sheets

(56) References Cited

U.S. PATENT DOCUMENTS

| | | | |
|---|---|---|---|
| 2013/0079026 A1* | 3/2013 | Hagedorn | H04W 4/027 |
| | | | 455/456.1 |
| 2013/0306726 A1* | 11/2013 | Wong | H02J 7/0029 |
| | | | 235/440 |
| 2015/0130613 A1* | 5/2015 | Fullam | G08B 21/043 |
| | | | 340/539.12 |
| 2015/0134358 A1* | 5/2015 | Fisher | G06F 19/00 |
| | | | 705/3 |
| 2015/0182130 A1* | 7/2015 | Utter, II | A61B 5/681 |
| | | | 600/483 |
| 2016/0034658 A1 | 2/2016 | Berman et al. | |
| 2016/0183854 A1* | 6/2016 | Lee | A61B 5/14514 |
| | | | 600/347 |
| 2020/0112340 A1* | 4/2020 | Roh | H04W 76/14 |
| 2020/0380494 A1* | 12/2020 | Wang | G07F 9/006 |

\* cited by examiner

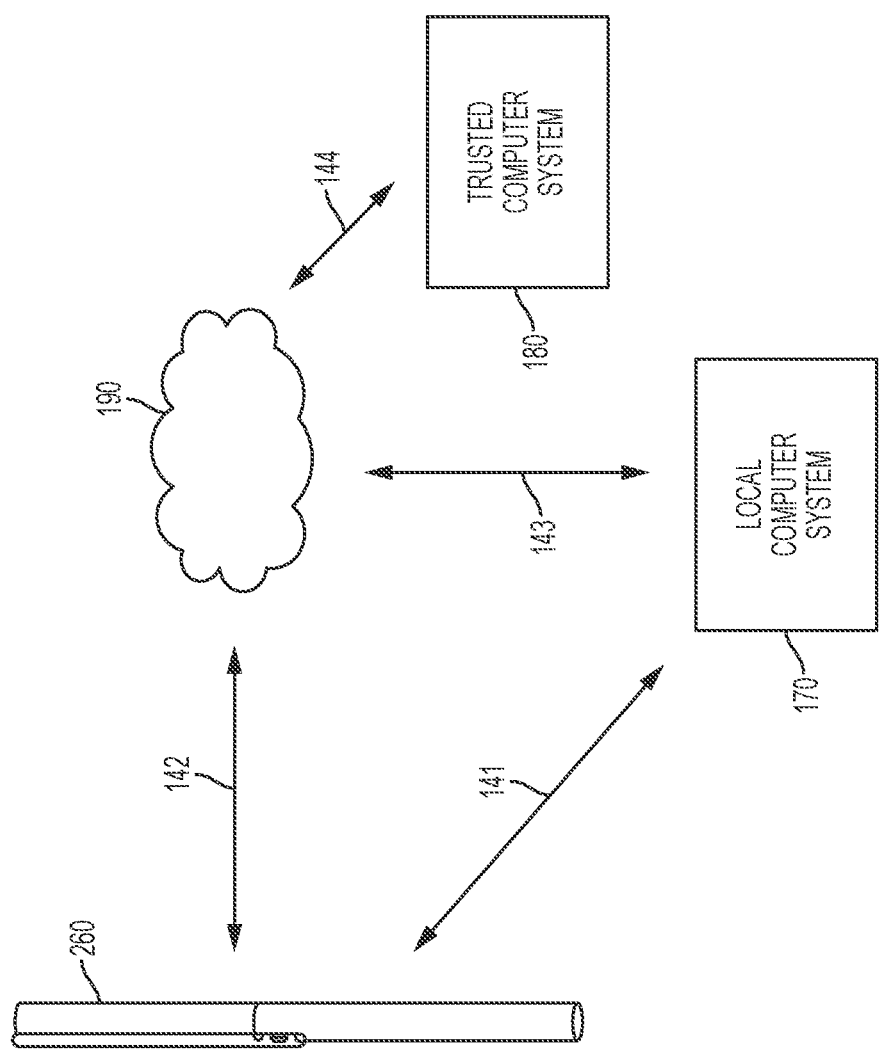
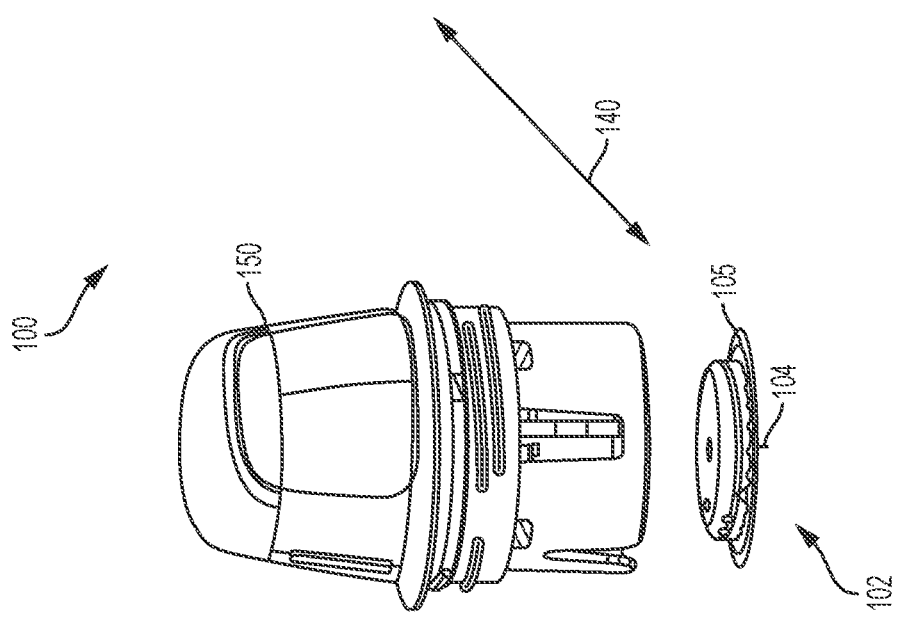
FIG. 1

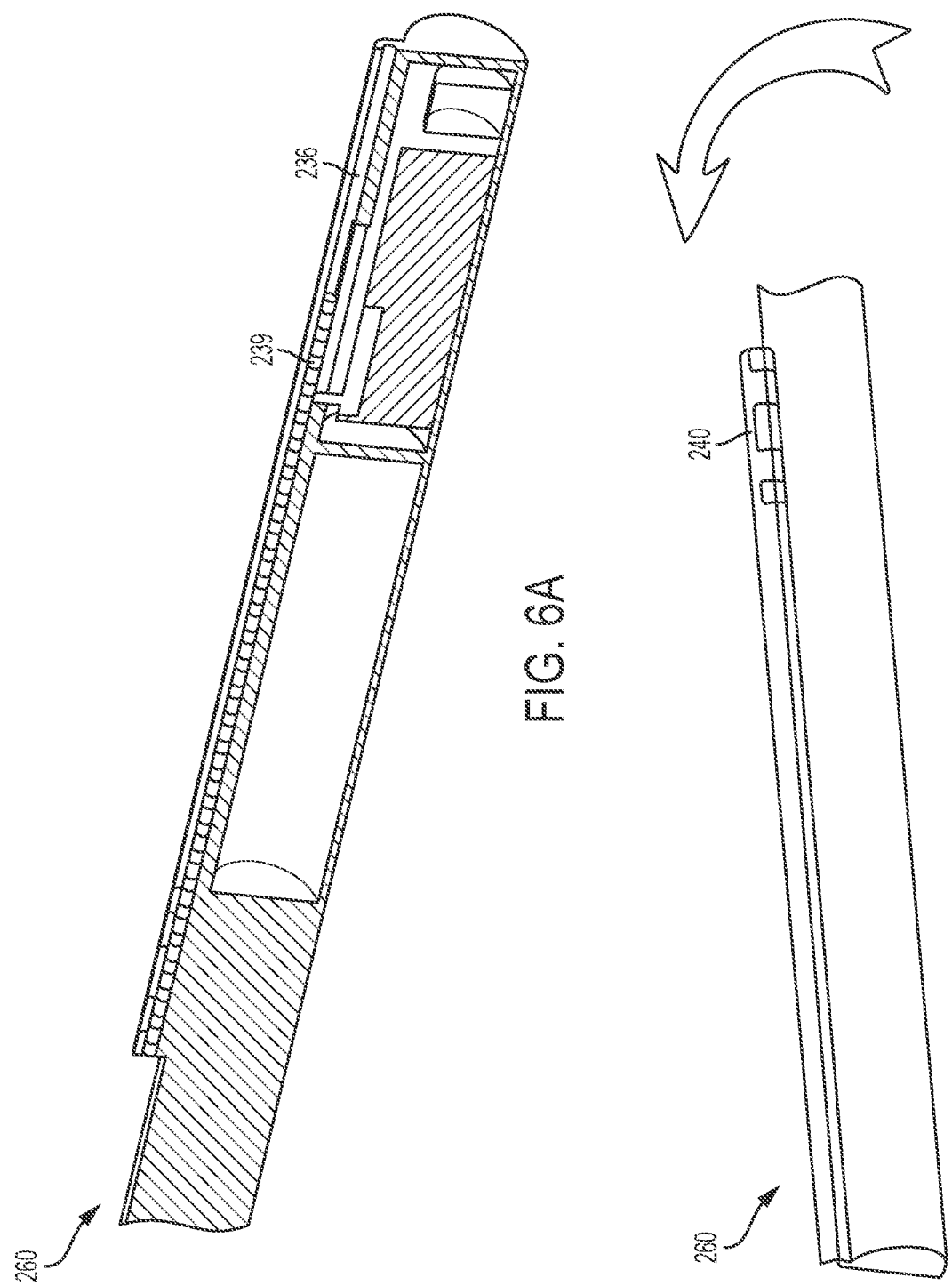

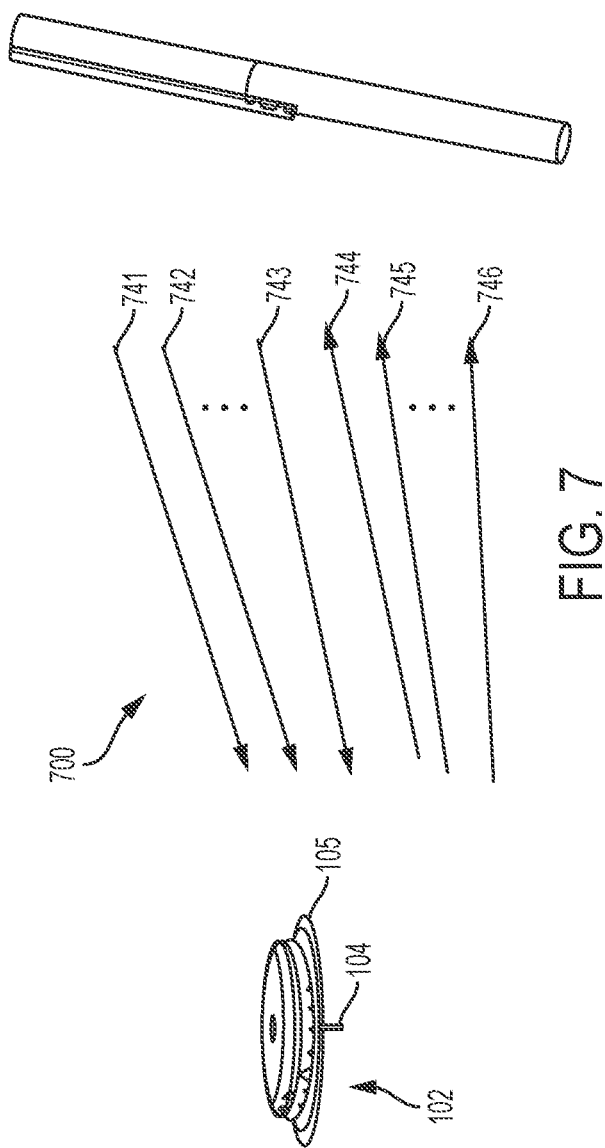

SYSTEMS, DEVICES, AND METHODS FOR INTEGRATION OF AN ANALYTE DATA READER AND MEDICATION DELIVERY DEVICE

CROSS-REFERENCE TO RELATED APPLICATIONS

The present application is a continuation of International Patent Application No. PCT/US2018/018232, filed Feb. 14, 2018, which claims priority to and the benefit of U.S. Provisional Patent Application No. 62/459,441, filed Feb. 15, 2017, both of which are incorporated by reference herein in their entirety for all purposes.

FIELD

The subject matter described herein relates generally to systems, devices, and methods for the integration of an analyte data reader and a medication delivery device, where the medication delivery device can have a compact form factor, such as with an insulin pen.

BACKGROUND

The detection and/or monitoring of analyte levels, such as glucose, ketones, lactate, oxygen, hemoglobin A1C, or the like, can be vitally important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including inconvenience, testing discretion, pain associated with glucose testing and cost.

For example, for diabetics that require the administration of insulin, glucose levels are typically measured by performing a blood glucose measurement with a test strip or by using a glucose sensor inserted into the body. Maintaining multiple and separate devices, however, for purposes of monitoring analyte levels and administering medication can be burdensome to the patient. In addition, a lack of interoperability between different devices used by diabetics can create further inconvenience, e.g., where the medication delivery device, reader device and sensor device are each manufactured by a different party. For instance, requiring the patient to manually input information from one device to another can be cumbersome and prone to human error.

For these and other reasons, needs exist for an integrated analyte data reader and medication delivery device.

SUMMARY

Provided herein are example embodiments of systems, devices and methods for the integration of an analyte reader and medication delivery device. Generally, an integrated analyte data reader and medication delivery device can be provided to an individual for the monitoring of one or more analyte levels of the individual, as well as the administering of medication such as insulin. The integrated analyte data reader and medication delivery device can have a small form factor, such as that of an insulin pen. In addition, the integrated analyte data reader and medication delivery device can communicate wirelessly with a sensor control device, also having a small form factor, that is worn on the individual's body. The sensor control device can include an in vivo analyte sensor for measuring an analyte level (or multiple analyte levels) in a subject, and can be configured such that at least a portion of the sensor is in contact with a bodily fluid of the subject. The sensor control device can also include communications circuitry for wirelessly transmitting data to the integrated analyte reader and medication delivery device.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 1 is a system overview of a sensor control device, integrated analyte data reader and medication delivery device, network, local computer system and trusted computer system.

FIGS. 6A-6B are perspective views depicting an example embodiment of an integrated analyte data reader and medication delivery device.

FIG. 7 is a system diagram depicting an example embodiment of a communication path between an integrated device and a sensor control device.

DETAILED DESCRIPTION

Figure 2A:
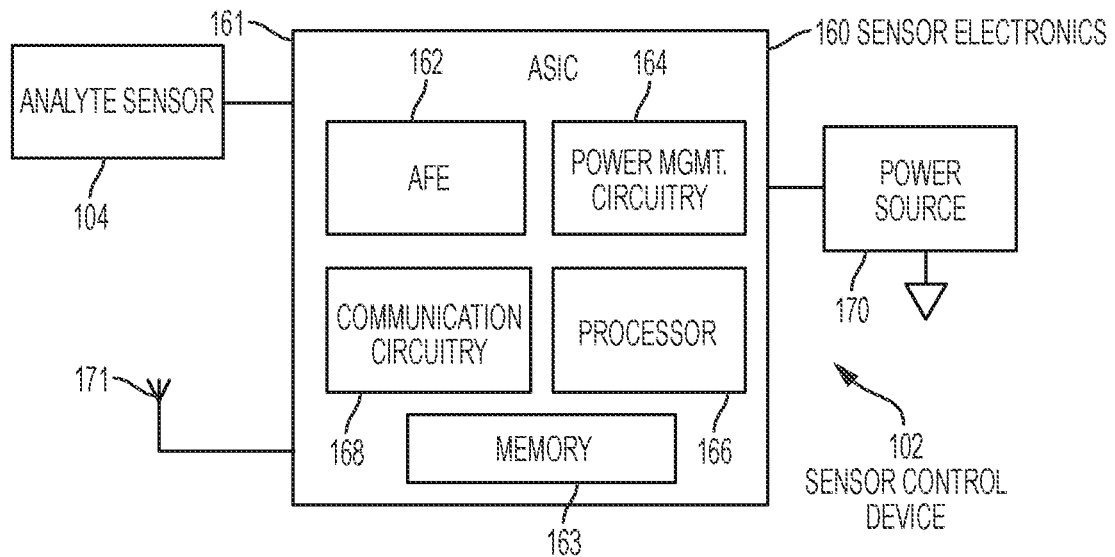
FIGS. 2A and 2B are block diagrams depicting example embodiments of sensor control devices.

Before the present subject matter is described in detail, it is to be understood that this disclosure is not limited to the particular embodiments described herein, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the integration of an analyte data reader and medication delivery device. In many embodiments, the integrated device can have a small form factor, such as that of an insulin pen. The integrated device embodiments disclosed herein can include communications circuitry for receiving data from sensor control devices (wirelessly and/or via a wire). In many embodiments, the sensor control device can include an analyte sensor configured so that at least a portion of the sensor is, or can be, positioned in the body of a user to obtain information about at least one analyte of the body, such as glucose, in a bodily fluid (e.g., subcutaneously within the interstitial fluid ("ISF") or blood, within the dermal fluid of the dermal layer, or otherwise). In some embodiments, for example, the sensor is configured to measure a glucose level. Additionally, the detection of other analytes is within the scope of the present disclosure, and can include, for example, ketones, lactate, oxygen, hemoglobin A1C, acetyl choline, amylase, bilirubin, cholesterol, chorionic gonadotropin, creatine kinase (e.g., CK-MB), creatine, DNA, fructosamine, glutamine, growth hormones, hormones, peroxide, prostate-specific antigen, prothrombin, RNA, thyroid stimulating hormone, troponin and others. The embodiments disclosed herein can also be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of integrated analyte data reader and medication delivery devices are disclosed, and these devices can have one or more antenna for wireless communications, non-transitory memories (e.g., for storing instructions and data), power sources, communication circuits, transmitters, receivers, processors and/or controllers (e.g., for executing instructions stored in memory) that can perform any and all method steps, or facilitate the execution of any and all method steps.

These embodiments and others described herein represent improvements in the field of computer-based analyte monitoring and medication delivery systems. For example, in some prior systems, analyte values would need to be transcribed into a separate device for dose calculation or for retrospective analysis. The embodiments disclosed herein can eliminate the need for multiple devices and therefore reduce the chance of transcription error. As another advantage, transferring glucose values to an integrated analyte reader and medication delivery device places the information where the focus needs to be—on the device where the resulting dose is to be delivered. Furthermore, the embodiments disclosed herein reduce the need to carry multiple devices (e.g., a separate reader or smartphone), particularly where a sensor capable of wireless communications is used, and thus increases convenience to the patient. Other improvements and advantages are provided, and will be apparent to those of skill in the art. The various configurations of these devices are described by way of the embodiments which are only examples.

Other features and potential advantages of the disclosed embodiments are further discussed below.

Before describing these aspects of the embodiments in detail, however, it is first desirable to describe examples of devices that can be present within the analyte monitoring and medication delivery system such as, for example, a sensor control device that transmits data measured with an in vivo analyte sensor, as well as examples of these devices' operation, all of which can be used with the embodiments described herein.

There are a number of types of systems which utilize in vivo analyte sensors. "Continuous Analyte Monitoring" systems (e.g., "Continuous Glucose Monitoring" systems), for example, can transmit data from a sensor control device to a reader device continuously or repeatedly with or without prompting, e.g., automatically according to a schedule. "Flash Analyte Monitoring" systems (e.g., "Flash Glucose Monitoring" systems or simply "Flash" systems), as another example, can transfer data from a sensor control device in response to a user-initiated request for data by a reader device (e.g., a scan), such as with a Near Field Communication (NFC) or Radio Frequency Identification (RFID) protocol. Some systems utilizing in vivo analyte sensors can also operate without the need for finger stick calibration.

In vivo analyte monitoring systems can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

Example Embodiments of In Vivo Analyte Monitoring Systems

FIG. 1 is a conceptual diagram depicting an example embodiment of an in vivo analyte monitoring system 100 that includes a sensor control device 102 and an integrated analyte data reader and medication delivery device 260 (also referred to herein simply as integrated device 260). System 100 can also include a sensor applicator 150, which can be used to apply sensor control device 102 to a monitoring location on a user's skin such that a sensor 104 is maintained in position in the user's body for a period of time by an adhesive patch 105. Sensor control device 102 is further described with respect to FIGS. 2A and 2B, and can communicate with integrated device 260 via a communication path 140 using a wired or wireless technique (or combination thereof). Example wireless protocols that can be used in path 140 (as well as paths 141-144 described herein) include Bluetooth, Bluetooth Low Energy (BLE, BTLE, Bluetooth SMART, etc.), Near Field Communication (NFC), Ultra High Frequency (UHF), Wi-Fi, and other wireless and RF communication protocols.

Bluetooth is a well-known standardized short range wireless communication protocol, and Bluetooth Low Energy is a version of the same that requires less power to operate. Bluetooth Low Energy (Bluetooth LE, BTLE, BLE) is also referred to as Bluetooth Smart or Bluetooth Smart Ready. A version of BTLE is described in the Bluetooth Specification, version 4.0, published Jun. 30, 2010. The terms "NFC" and "UHF" apply to a number of protocols (or standards) that set forth operating parameters, modulation schemes, coding, transfer speeds, frame format, and command definitions for, respectively, NFC and UHF devices. The following is a non-exhaustive list of examples of these protocols: ECMA-340, ECMA-352, ISO/IEC 14443, ISO/IEC 15693, ISO/IEC 16000-3, ISO/IEC 18092, ISO/IEC 21481, ISO 18000-1, ISO 18000-2, ISO 18000-3, ISO 18000-4, ISO 18000-6a, ISO 18000-6b, ISO 18000-6C, and ISO 18000-7.

Communication across communication path 140 can be direct from sensor control device 102 to integrated device 260 without an intermediary. In alternative embodiments, sensor control device 102 can communicate to integrated device 260 indirectly through an intermediary, e.g., by communicating to a first device that then communicates to integrated device 260. That first device can be, e.g., a display device or data processing module as described in U.S. Patent Publication No. 2011/0213225 (the '225 Publication), which is incorporated by reference herein in its entirety for all purposes.

Individuals can monitor and administer medication using integrated device 260, which can also communicate with local computer system 170 via a communication path 141 using a wired or wireless technique. Local computer system 170 can include one or more of a laptop, desktop, tablet, phablet, smartphone, set-top box, video game console, or other computing device. Local computer system 170 can also communicate via communications path 143 with a network 190 using a wired or wireless technique (or combination thereof). Network 190 can include any of a number of networks, such as private networks and public networks, local area or wide area networks, and so forth. Network 190 can be the cloud. A trusted computer system 180 can include a server and can provide authentication services and/or secured data storage and can communicate via communications path 144 with network 190 by a wired or wireless technique (or combination thereof). Trusted computer system 180 can be considered part of network 190 (or the cloud) when considered from the perspective of devices 102, 120, and 170. Communication across communication paths 141-144 can be direct or indirect.

Example Embodiments of Sensor Control Devices

Figure 2B:
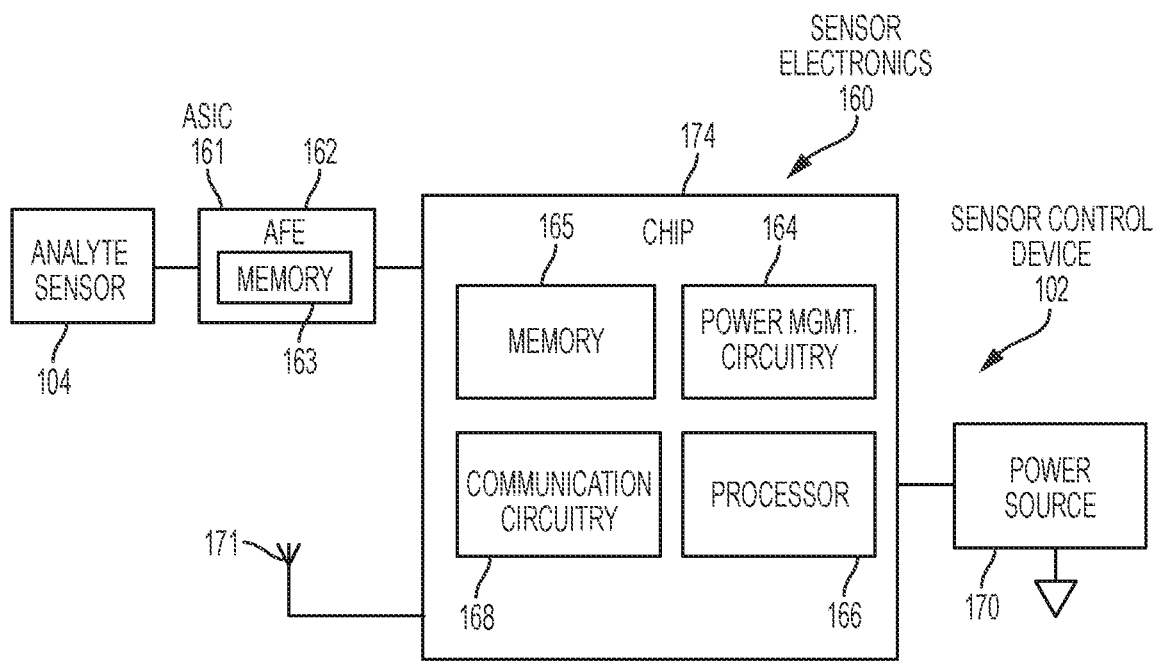

FIGS. 2A and 2B are block diagrams depicting example embodiments of sensor control devices 102 each including an analyte sensor 104 and sensor electronics 160 (including analyte monitoring circuitry) that, collectively, can have the majority of the processing capability for rendering end-result data, such as analyte metrics, which are suitable for display to the user. In FIG. 2A, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as in vivo analyte monitoring circuitry, but in other embodiments either circuit can perform the monitoring functions. Processor 166 can include one or more processors, microprocessors, controllers, and/or microcontrollers, each of which can be a discrete chip or distributed amongst (and a portion of) a number of different chips. Communications circuitry 168 can be capable of wireless communications according to a standard wireless protocol, an RF communications protocol (e.g., Bluetooth, Bluetooth Low Energy, NFC, UHF, WiFi, etc.), or a proprietary wireless protocol.

A non-transitory memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form. Processor 166, in turn, can execute one or more instructions stored in memory 163, which can cause processor 166 to process the data which, in turn, can then be provided to communication circuitry 168 for sending, by way of antenna 171, to device 260 (not shown).

FIG. 2B is similar to FIG. 2A, but instead depicts two discrete semiconductor chips 162 and 174, which can be packaged together or separately. Here, AFE 162 is resident on ASIC 161. As shown here, AFE 162 is coupled to analyte sensor 104. Referring to chip 174, processor 166 is integrated with power management circuitry 164 and communication circuitry 168 on chip 174. AFE 162 includes memory 163 and chip 174 includes memory 165, which can be isolated or distributed within. In one example embodiment (not shown), AFE 162 is combined with power management circuitry 164 and processor 166 on one chip, while communication circuitry 168 is on a separate chip. In another example embodiment (also not shown), both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

In some embodiments, sensor control device 102 collects raw measurement data from the body and transmits that raw data (with or without signal conditioning, and with or without other data such as temperature data) to integrated device 260 for further algorithmic processing into a format representative of the wearer's analyte levels, which can then be displayed (or made displayable) by integrated device 260. In other embodiments, that algorithmic processing is performed by sensor control device 102 prior to transmission to integrated device 260.

Figure 3A:
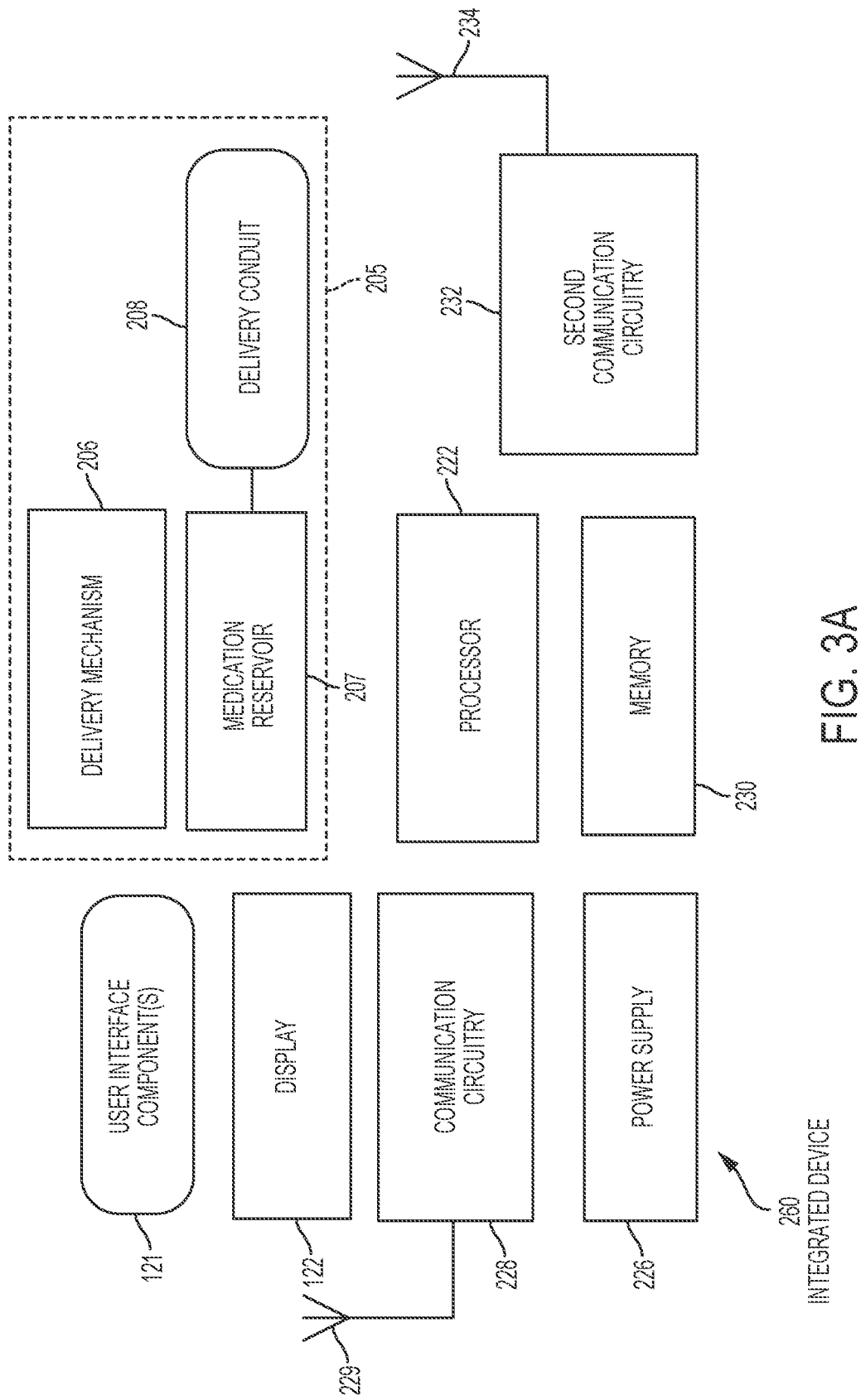
FIG. 3A is a block diagram depicting an example embodiment of an integrated analyte data reader and medication delivery device.

Example Embodiments of Integrated Analyte Data Reader and Medication Delivery Devices FIG. 3A is a block diagram depicting an example embodiment of integrated analyte data reader and medication delivery device 260. Here, integrated device 260 can include a display 122, one or more user interface components 121, a processor 222, non-transitory memory 230, communication circuitry 228 (which in some embodiments is NFC, UHF or other RF communications circuitry) coupled with an antenna 229, and a power supply 226. Second communication circuitry 232 can also be included, which can be coupled with an antenna 234, and can communicate according to one or more other communication protocols such as Wi-Fi, Bluetooth, BTLE, ANT+, GPS, and others. As understood by one of skill in the art, these components can be electrically and communicatively coupled in a number of different manners.

Integrated device 260 can also include medication delivery portion 205 for the delivery of a medication, which can include a delivery mechanism 206 coupled with a medication reservoir 207, which is, in turn, coupled with a delivery conduit 208. Medication delivery portion 205 is capable of injecting or infusing a medication or drug, such as but not limited to insulin, into the body of the individual wearing sensor control device 102. Delivery conduit 208 can include an introducer (e.g., a needle) or an infusion cannula for insertion into the individual's body. The introducer can be coupled with the medication reservoir 207 (either directly or through an intermediary conduit such as tubing) responsible for storing the medication to be delivered.

Delivery mechanism 206 can be, for example, a pump configured to force the medication from reservoir 207, through conduit 208 and into the body. Medication delivery portion 205 can be configured in a manner similar to an insulin delivery pen, an automated wearable infusion pump (such as a basal delivery pump), and the like. In some embodiments, for example, delivery mechanism 206 can be manual (or partially manual), and can require a user to apply a manual force or pressure to a button or trigger to initiate the injection of medication.

Integrated device 260 can store instructions, executable by processor 222, that operate delivery mechanism and/or reservoir 207 to control the amount of insulin delivered. These instructions can also cause calculation of insulin delivery amounts and durations (e.g., a bolus infusion and/or a basal infusion profile) based on analyte level measurements obtained directly or indirectly from sensor control device 102. Alternatively, calculations of insulin delivery amounts and durations, and the control of the medication delivery portion, can be performed by a separate computing device. When medication delivery portion 205 is configured as an automated pump, then integrated device 206 can operate as a closed loop or semi-closed loop system. In many embodiments, medication delivery portion 205 is configured like a compact form factor manual injection device (such as a pen), and integrated device 260 operates as part of an open loop medication delivery system, requiring user interaction each time medication delivery is required.

Figure 3B:
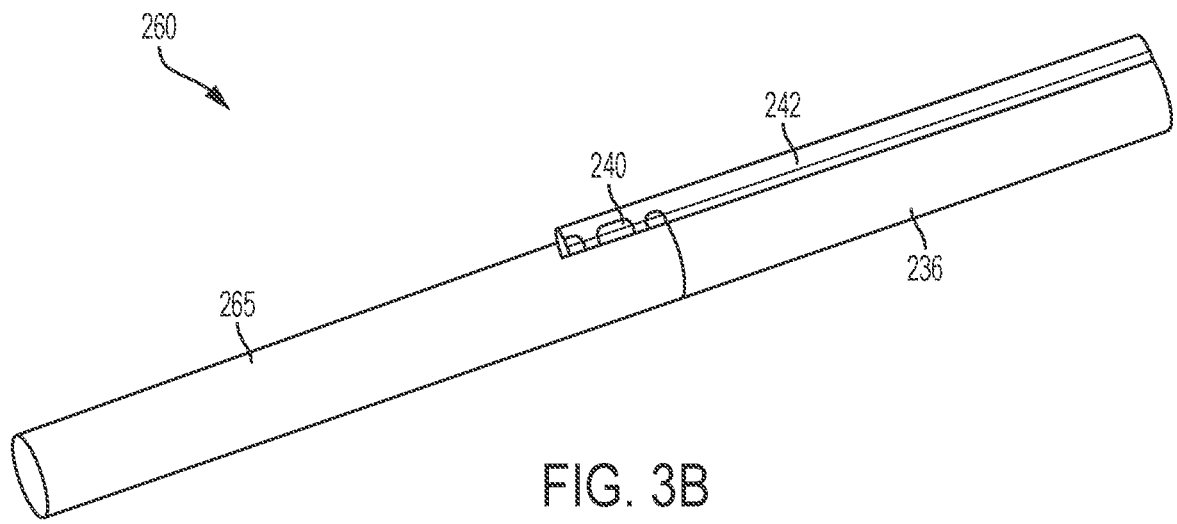
FIG. 3B-3C are perspective views depicting an example embodiment of an integrated analyte data reader and medication delivery device.
Figure 3C:
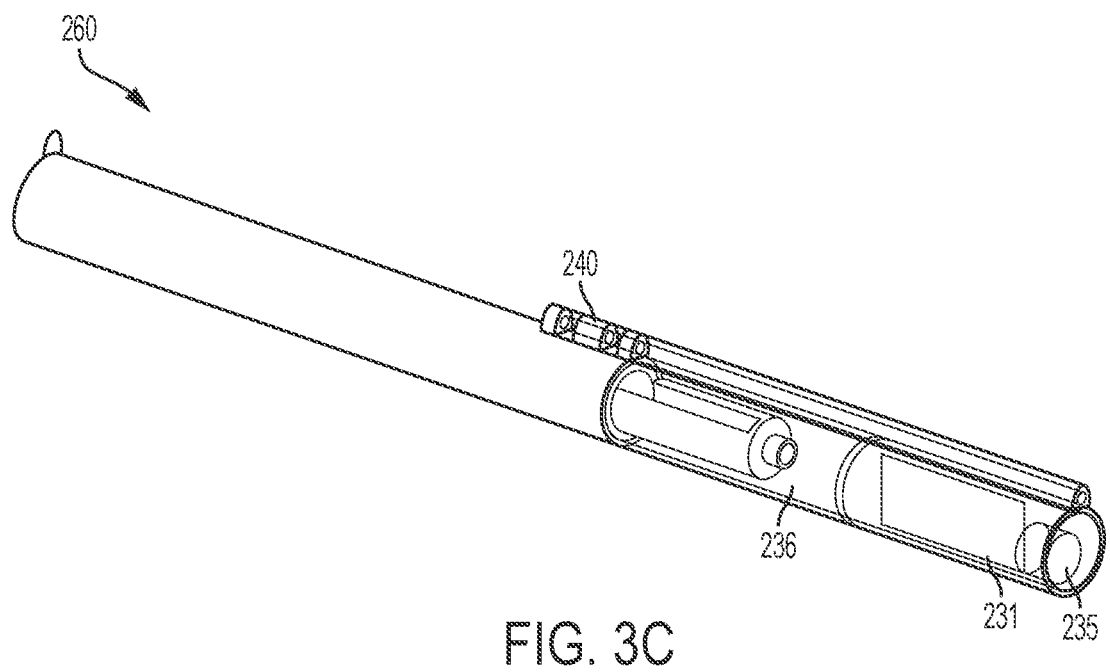

FIGS. 3B and 3C are perspective views of an example embodiment of an integrated analyte data reader and medication delivery device 260, shown here as an insulin pen. Referring to FIG. 3B, integrated device 260 can include a cylindrical housing having a body portion 265 and a removable cap 236. In other embodiments, the housing of integrated device 260 can have a semi-cylindrical shape and/or include, for example, an elliptical, square, rectangular or polygonal cross-section. In some embodiments, cap 236 can be further secured to body 265 by a post (not shown) disposed inside a post housing 242. Post housing 242 can be coupled to cap 236 at a first end portion, and can also be coupled to body 265 at a second end portion that includes a hinge 240. Various example mechanisms by which cap 236 can be secured to body 265 by post and post housing 242 are described herein with respect to FIGS. 6A and 6B.

Turning to FIG. 3C, integrated device 260 is shown with a semi-transparent perspective view. In some embodiments, cap 236 can include electronics, such as those described with respect to FIG. 3A, including, for example, a printed loop antenna on a standard fiberglass printed circuit board 231 and/or a rechargeable coin-cell battery 235.

Referring back to FIG. 3A, antenna 229 can be an NFC loop antenna. In all of the embodiments described herein, loop antenna 229 can be shaped in an ellipsoidal or circular fashion (see, e.g., FIG. 4C) or a polygonal fashion (see, e.g., FIG. 5B). Loop antenna 229 can have a diameter, wire width, and number of turns (e.g., 1, 2, 3, 4, 5, 6, etc.) as desired for the specific application. For example, in certain embodiments, loop antenna 229 can have an outer diameter that is at least that of a quarter or as large as two times the outer diameter of a quarter or larger, which is a diameter range of 0.955 inches (2.43 centimeters (cm)) to 1.91 inches (4.86 cm) or more. The embodiments disclosed herein are not limited to this range, as other sizes are within the scope of this disclosure. In some embodiments, antenna 229 can have approximately twice the outer diameter of the corresponding antenna in sensor control device 102 (or the blood glucose meter). This configuration can facilitate wireless communications between integrated device 260 and the device to be scanned (e.g., sensor control device 102), while requiring less specificity in orientation, distance and placement of the respective antennas.

FIGS. 4A-4C and 5A-5E depict example embodiments of antenna 229, and their respective configurations. Those of skill in the art will understand that the embodiments and their respective configurations are illustrative and are not meant to be limiting in any way. In particular, four example embodiments of antenna 229 are described below in further detail and with reference to FIGS. 4A-4C and 5A-5E.

Example Embodiments of Antennas on Flat Surfaces of a Pen or Pen Cap

Figure 4A:
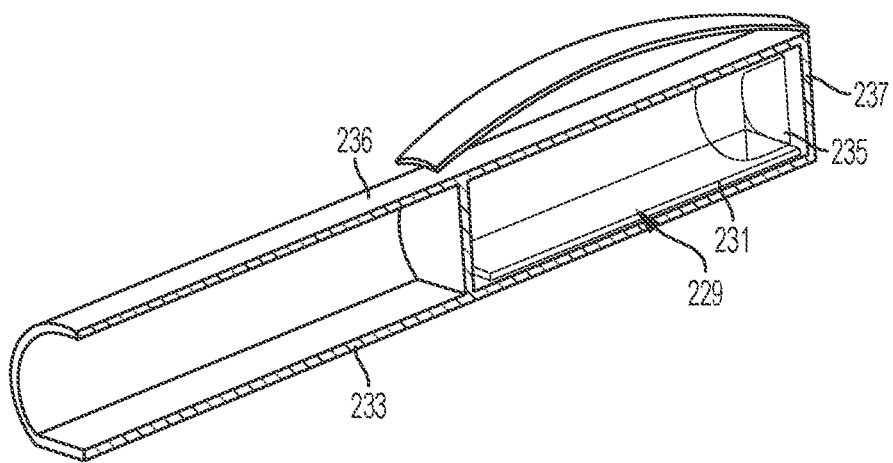
FIGS. 4A-4C are perspective views depicting example embodiments of antennas.

FIG. 4A is a perspective cutaway view of one example embodiment of antenna 229. Antenna 229 can be coupled with at least one substantially flat side 233 of an insulin pen cap 236 having at least one substantially flat side 233. Cap 236 can be removable from the main housing of integrated device 260 (not shown) to expose the introducer or needle (not shown). In some embodiments, a cross-section of cap 236 can have a "D" shaped profile. In other embodiments, cap 236 can have multiple flat sides, and multiple antennas 229 can be positioned on the different flat sides. These configurations can provide a convenient planar surface for antenna placement. In some embodiments, this can be a relatively low-cost antenna implementation, such as can be achieved by inclusion of a printed loop antenna 229 on a standard fiberglass printed circuit board 231. Antenna 229 can be coupled (directly or indirectly) with the interior surface of flat side 233 as shown here, or on an exterior surface of flat side 233. In some embodiments, antenna 229 can be embedded or encapsulated within flat side 233. In addition, flat side 233 of cap 236 can also provide tactile feedback to the user to aid in placing antenna 229 near the device to be read, e.g., sensor control device 102. In other embodiments, cap 236 can have more than one substantially flat side 233, which can provide multiple surfaces for multiple antennas 229 (such as a dual antenna configuration) . A rechargeable battery 235, for example a cylindrical coin-cell type battery, can be positioned at an end portion 237 near the terminus of cap 236. Although FIG. 4A depicts antenna 229 coupled with an insulin pen cap 236, in other embodiments, antenna 229 can be coupled instead with a substantially flat side of the housing of integrated device 260.

Example Embodiments of Dual Antennas on a Pen or Pen Cap

Figure 4B:
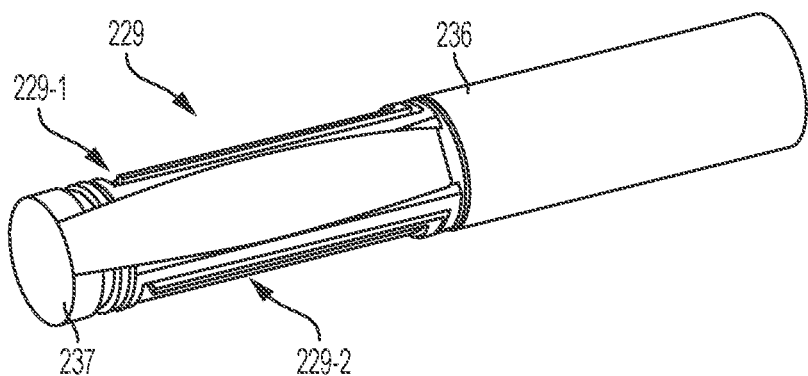

FIG. 4B is a perspective view of another example embodiment of a cap 236 for a pen-type device 260 where antenna 229 has a dual configuration with antennas 229-1 and 229-2. Dual antennas 229-1 and 229-2 can be positioned on an exterior surface of cap 236 as shown here, or can be positioned on an exterior surface outside of the main housing for device 260 (not shown). In other embodiments, dual antennas 229-1 and 229-2 can be positioned on an interior surface within the cavity of cap 236 or within the main housing of device 260. In some cases, antennas 229-1 and 229-2 are positioned within a side wall of device 260 or cap 236. In all embodiments, the surface with which antennas 229-1 and 229-2 are coupled (indirectly or directly) can be curved (such as shown here) or flat (e.g., as described with respect to FIG. 4A).

A dual antenna configuration can provide more flexibility in that antenna 229 need not be oriented with a great degree of specificity relative to the device to be read, e.g., sensor control device 102. For example, in some embodiments, integrated device 260 can be held in almost any orientation relative to the device to be read, and still produce enough coupled field to perform the read function. The two antenna loops 229-1 and 229-2 are driven in phase so the field from the two loops is additive. Although in this embodiment loops 229-1 and 229-2 follow the curve of the outer surface of cylindrical pen cap 236, there is sufficient field produced even where the two loops come closest to each other. As with the flat-sided cap configuration (FIG. 4A), the dual antenna configuration can include a power source, such as a battery 235, along with the electronics for integrated analyte data reader and medication delivery device 260 in a cylindrical space at an end portion 237 of pen cap 236. The cylindrical shape is a common one for batteries.

Example Embodiments of Pens with Enlarged Ends for Antennas

Figure 4C:
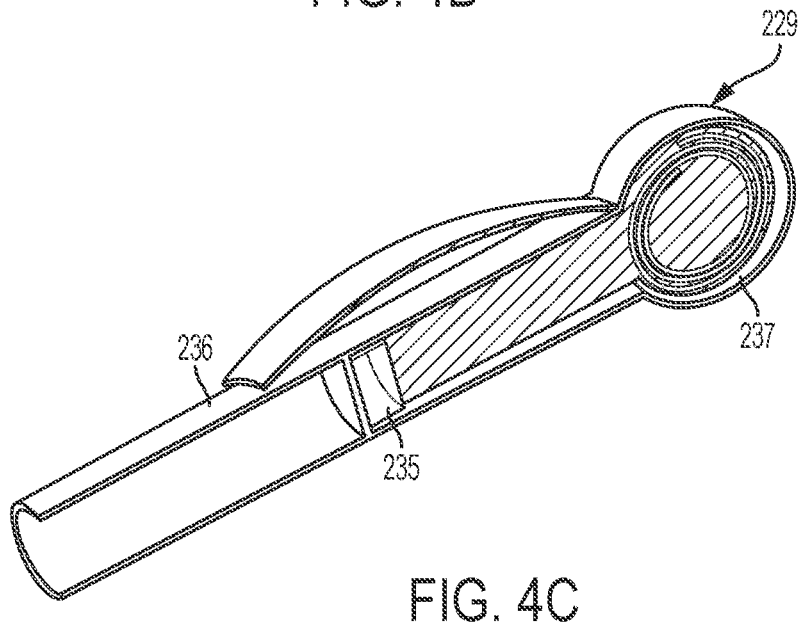

FIG. 4C is a perspective cutaway view of another example embodiment of antenna 229, having an enlarged end portion 237 that includes an antenna 229. Enlarged end portion 237 has a width that is greater than the remainder of the body of device 260, giving the end a bulbous shape. In some cases, device 260 with enlarged end portion 237 is referred to as a lollipop shape. In this embodiment, end portion 237 is on cap 236 although in other embodiments, enlarged end portion 237 can be at the end of device 260 without cap 236. Alternatively, the enlarged portion 237 can be at an intermediate location such that a substantial length of the opposite ends of device 260 each have a width less than the enlarged portion. Although end portion 237 is shown in FIG. 4C as having a spherical or semi-spherical shape, other geometries can be utilized, including but not limited to, a conical shape, a tapered end shape, a pyramidal shape, a cylindrical or semi-cylindrical shape, or other like shape or configuration in which antenna 229 can be spatially segregated from battery 235 and other electronics. In some embodiments, the portion of integrated device 260 that is furthest away from end portion 237 has an elongate shape with a substantially constant width. These antenna configurations can allow the main body of device 260 to have a relatively small width and compact form factor, while permitting placement of antenna 229 away from the electronics and battery 235 that can be positioned elsewhere in device 260, such as in the opposite part of cap 236. These metallic components of the electronics and battery can reduce the effectiveness of antenna 229 if placed within its loop or near its perimeter.

Example Embodiments with Deployable Antennas

Figure 5A:
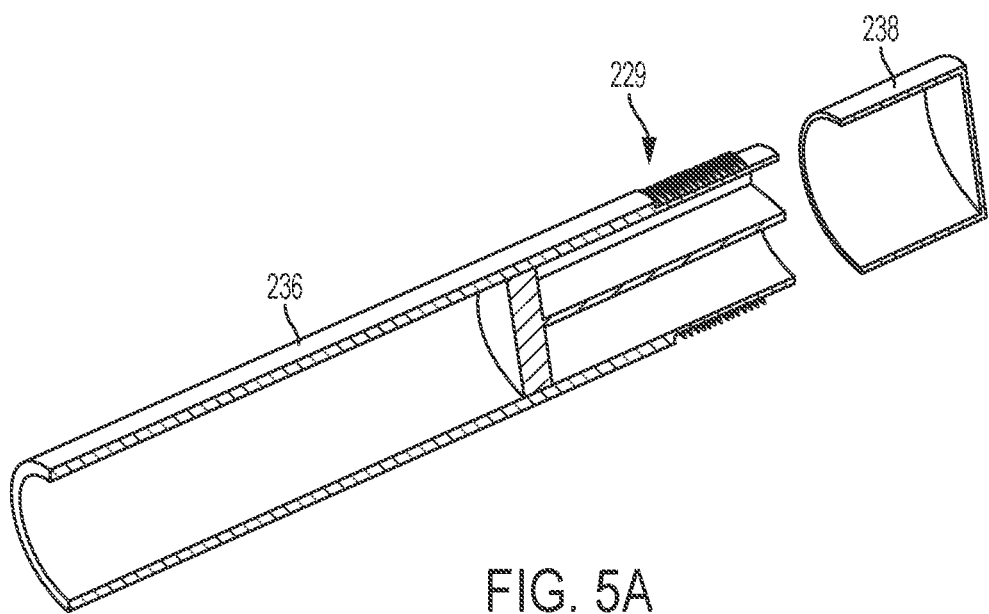
FIGS. 5A-5B are perspective cutaway views depicting example embodiments of antennas.

FIGS. 5A-5E depict perspective cutaway views of example embodiments of antennas 229. As shown in FIG. 5A, in some embodiments, antenna 229 can be wrapped around an outer portion of cap 236. Antenna 229 can be wrapped completely or partially around an outer surface of cap 236, which can also include an indentation in a portion of the outer surface around which antenna 229 is wrapped. Antenna 229 can consist of one or more wires or, in the alternative, can be formed of a flexible film substrate which can be wrapped around the outer surface of cap 236. A removable cover 238 can also be configured to enclose antenna 229 when the integrated device 260 is not in use.

Figure 5B:
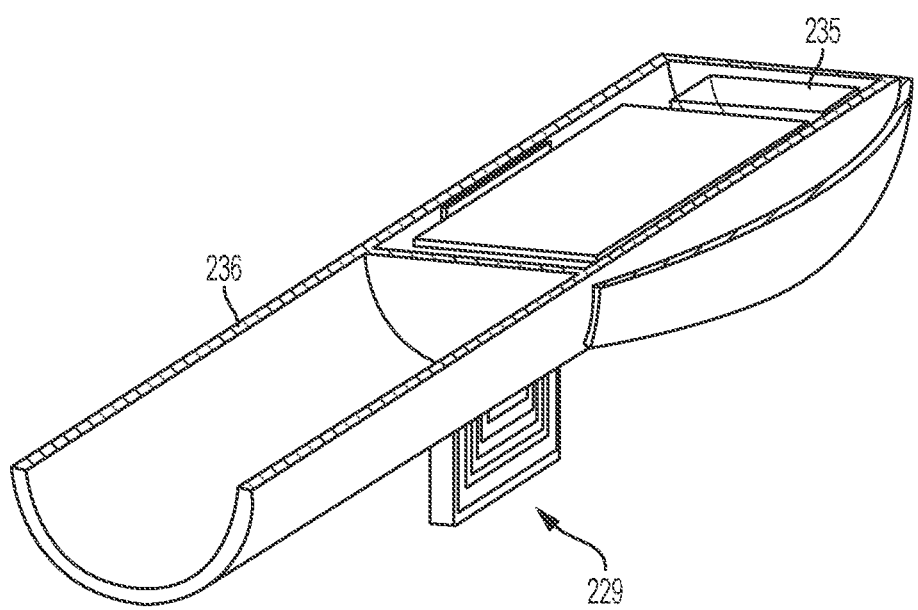
Figure 5C:
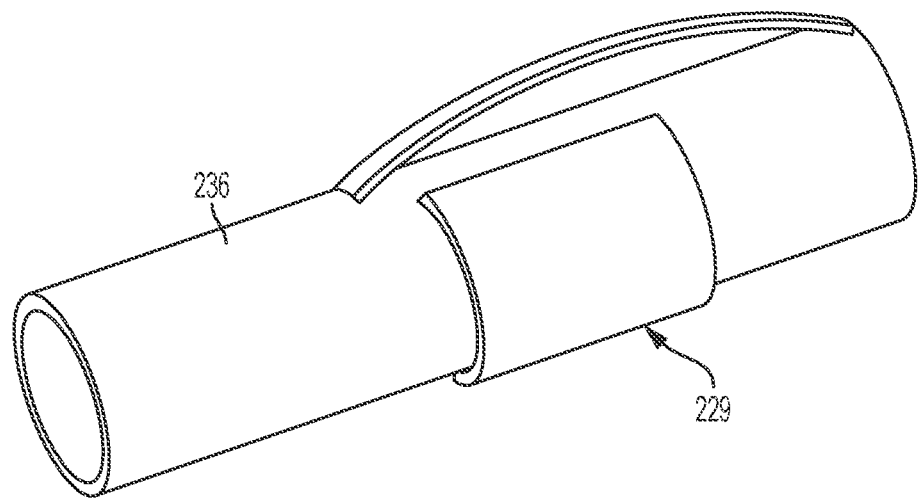
FIGS. 5C-5E are perspective cutaway views depicting an example embodiment of an antenna in different configurations.
Figure 5D:
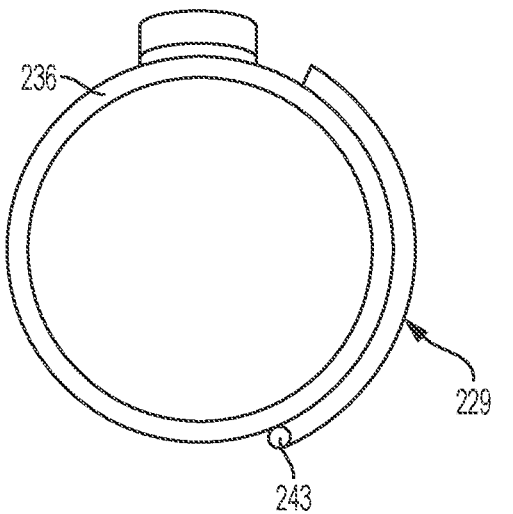
Figure 5E:
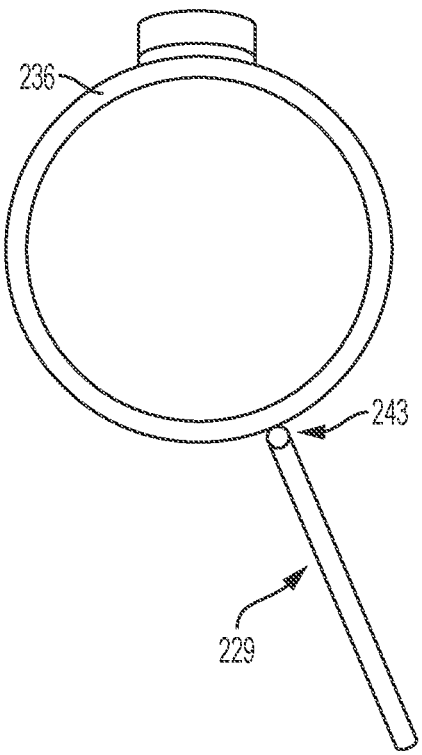

FIGS. 5B-5E depict another example embodiment of antenna 229, in which antenna 229 can be moved from an undeployed state (FIGS. 5C and 5D) to an extended or deployed state (FIGS. 5B and 5E). As seen in FIGS. 5C and 5D, in an undeployed state, antenna 229 can be disposed within or alongside cap 236 in a position that can be near to, or in close proximity to, other metallic components such as electronics. Antenna 229 can be embedded or printed upon a flexible sheet or film that is wound, wrapped, or curled one or more times around cap 236. In some embodiments, antenna 229 can be coupled to a hinge 243 disposed on an outer surface of cap 236, around which antenna 229 can pivot from an undeployed state to an extended or deployed state. In some embodiments, antenna 229 can also be retained in an undeployed (e.g., furled) state by another mechanism, for example, by an elastic band, slidable clip, or a compartment that can be slidably or hingeably opened. As shown in FIGS. 5B and 5E, during use, antenna 229 can be unfurled, like a flag, from around cap 236. In this manner, the unfurled antenna 229 extends away from cap 236 and the electronics and other metallic components contained therein, and can be size-optimized. In some embodiments, a top perimeter portion of the antenna "flag" 229 can include a spring material, which can be slightly bent back to stiffen the antenna 229 in an extended position and to hold antenna 229 in place for a scan operation. Additionally, the folding out of antenna 229 can automatically initiate the tag detection emissions from antenna 229. For example, in some embodiments, the unfurling of antenna 229 can be detected by a light sensor underneath antenna 229, or by a magnet and reed switch arrangement, or by a normally open button switch.

The swipe motion typical of what a user would do to initiate a scan by pen-type device 260 of a sensor control unit placed on his or her body (e.g. arm or abdomen) is distinguishable from other typical motions experienced by the pen, such as walking, driving, jumping. In each of the embodiments described herein, an accelerometer can be disposed within cap 236 of integrated device 260. The accelerometer can be coupled to the electronics, e.g., processor, memory, analog-to-digital converter, etc., within integrated device 260. The accelerometer can be configured to sense a "swiping" motion that is typical of the type of action a user would take to read a sensor control device 102 placed on his or her body (e.g., arm or abdomen). In this manner, in those embodiments that include an accelerometer, integrated device 260 need not have a button or switch for activating the NFC scan function prior to scanning sensor control device 102 (or other device). Furthermore, because accelerometers consume relatively little power, i.e., typically less than a hundred microwatts, they can always be on and able to sense the swipe gesture, yet consume significantly less power than a system driving the NFC antenna to scan for the sensor control device.

Example Embodiments of Adverse Condition Protection Features

Integrated device 260 can also store instructions, executable by processor 222, that operate to mitigate the risk of a harmful medication injection when an adverse condition is present in the subject. For example, the injection of insulin when a user has a low glucose level (e.g., below 55 mg/dL) can be particularly dangerous because it can cause a diabetic person to fall into a coma. Therefore, it is desirable for integrated device 260 to include one or more adverse condition protection features to warn the user in various ways that injecting insulin is dangerous when an adverse condition is present, or to prevent the insulin injection itself. These adverse condition protection features, which are described in further detail below, can include requiring one or more sensor control device scans before injection, displaying a warning indicator, preventing the removal of the insulin pen cap, inhibiting the depressing of the injection button, or any of the other features or combinations of features, as described herein.

In some example embodiments, integrated device 260 can store instructions in memory, executable by processor 222, that cause an indication to be output to the user that a sensor control device scan should be performed before injecting insulin. This feature can be initiated by sensing that cap 236 has been removed without having scanned the sensor control device 102, for example, within a predetermined time interval. In some embodiments, the removal of cap 236 can be detected, for example, by an accelerometer disposed in cap 236, and configured to detect the movement of cap 236 in a particular direction relative to integrated device 260. In other embodiments, the removal of cap 236 can be detected by a light sensor positioned on an area of the integrated device 260 that is covered by cap 236 when in place on device 260. In other embodiments, the removal of cap 236 can be detected by a magnetic switch (such as a reed switch). In other embodiments, removal can be detected by a mechanical-electrical switch, such as a switch biased towards an extended position and held in a depressed position by cap 236, where removal of cap 236 causes the switch to extend and trip the circuit (e.g., by closing or opening the circuit). Other methods of cap removal detection are contemplated and will be apparent to those of skill in the art. Upon sensing this condition, the user could be warned audibly, visually, haptically (e.g., with a vibration) or with another indicator.

Similarly, when the sensor control device is scanned, and an adverse condition is detected, e.g., the value is below a predetermined recommended low glucose threshold, a warning indicator can be visually illuminated on a prominent location of the integrated device 260. In some embodiments, an audible and/or vibratory signal can also be output to the integrated device 260.

According to another aspect of the embodiments, integrated device 260 can include one or more lock-out mechanisms that can be activated in response to a determination of an adverse condition, based on a sensor control device scan, finger stick measurement, or in response to an indication or alert associated with an adverse condition, where the indication or alert is received from another device, such as sensor control device 102. In some embodiments, for example, the lock-out mechanism can be a latch that is activated on device 260 to secure cap 236 to the main body of device 260, or otherwise prevent exposure of the introducer. The electronics and/or mechanism for the latch can be housed within cap 236 or the opposite portion (e.g., main body) of device 260. The latch can secure cap 236 to device 260 for a predetermined amount of time, during which time the user can be sufficiently warned that injecting insulin may be dangerous. According to some embodiments, a mechanical manual override can be optionally provided. In another embodiment, the lock-out mechanism can inhibit the operation of the injection button on device 260, so that insulin cannot be injected. Again, the lock-out mechanism can be configured to persist for a predetermined amount of time, to persist until a scan is performed to confirm an absence of an adverse condition, and/or to include a manual override mechanism.

FIGS. 6A and 6B are perspective cutaway views of an example embodiment of an adverse condition protection feature having a lock-out mechanism, such as the aforementioned latch. As depicted in FIG. 6A, a post or strut 239 disposed within integrated device 260 can be actuated with a solenoid or other actuator. The solenoid can be controlled by software stored in memory 230 and executed by processor 222 of device 260. Post 239 can be selectively moved into the interleaved hinges 240, as shown in FIG. 6B, which prevents cap 236 from rotating to a position that allows it to be removed. In this regard, post 239 can be configured as a deadbolt latch in some embodiments. In other embodiments, post 239 can be configured to engage a latch, hook, loop or aperture in cap 236 (not shown) to prevent cap 236 from being separated from integrated device 260. Conversely, post 239 can be removed after a predetermined time has elapsed, after an override feature has been engaged by the user, after a new reading indicates the low glucose level is no longer present, or otherwise. In some embodiments, post 239 can be spring loaded to allow a user to manually override the engaged position.

Figure 6C:
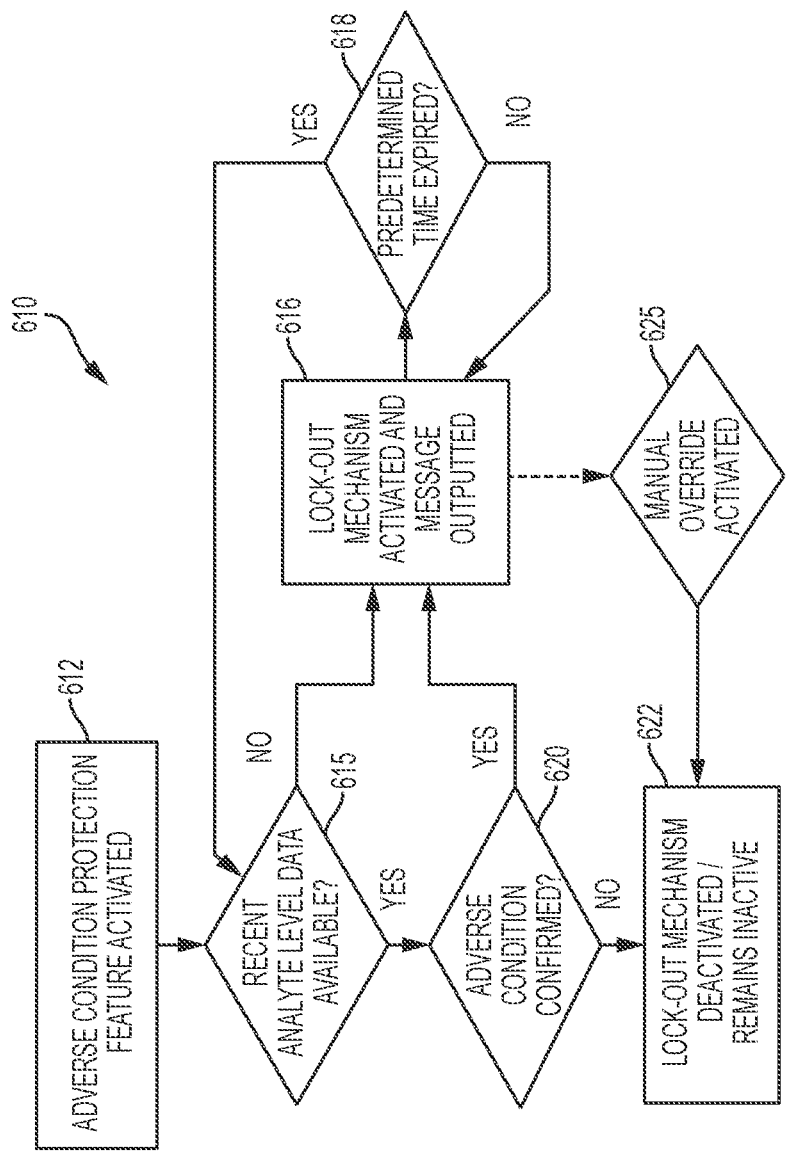
FIGS. 6C-6E are flow charts of example embodiments of methods for an adverse condition protection feature.
Figure 6D:
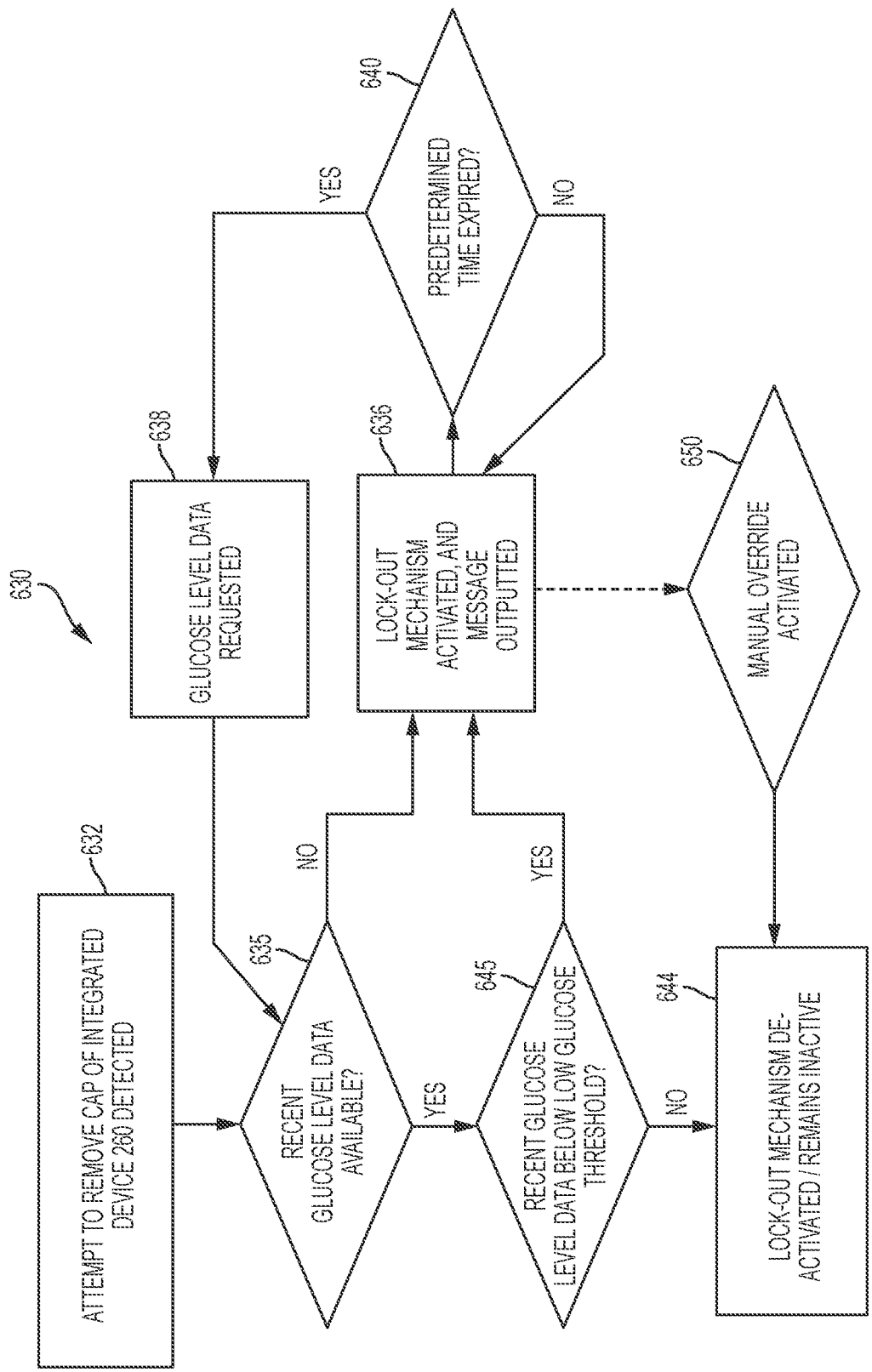
Figure 6E:
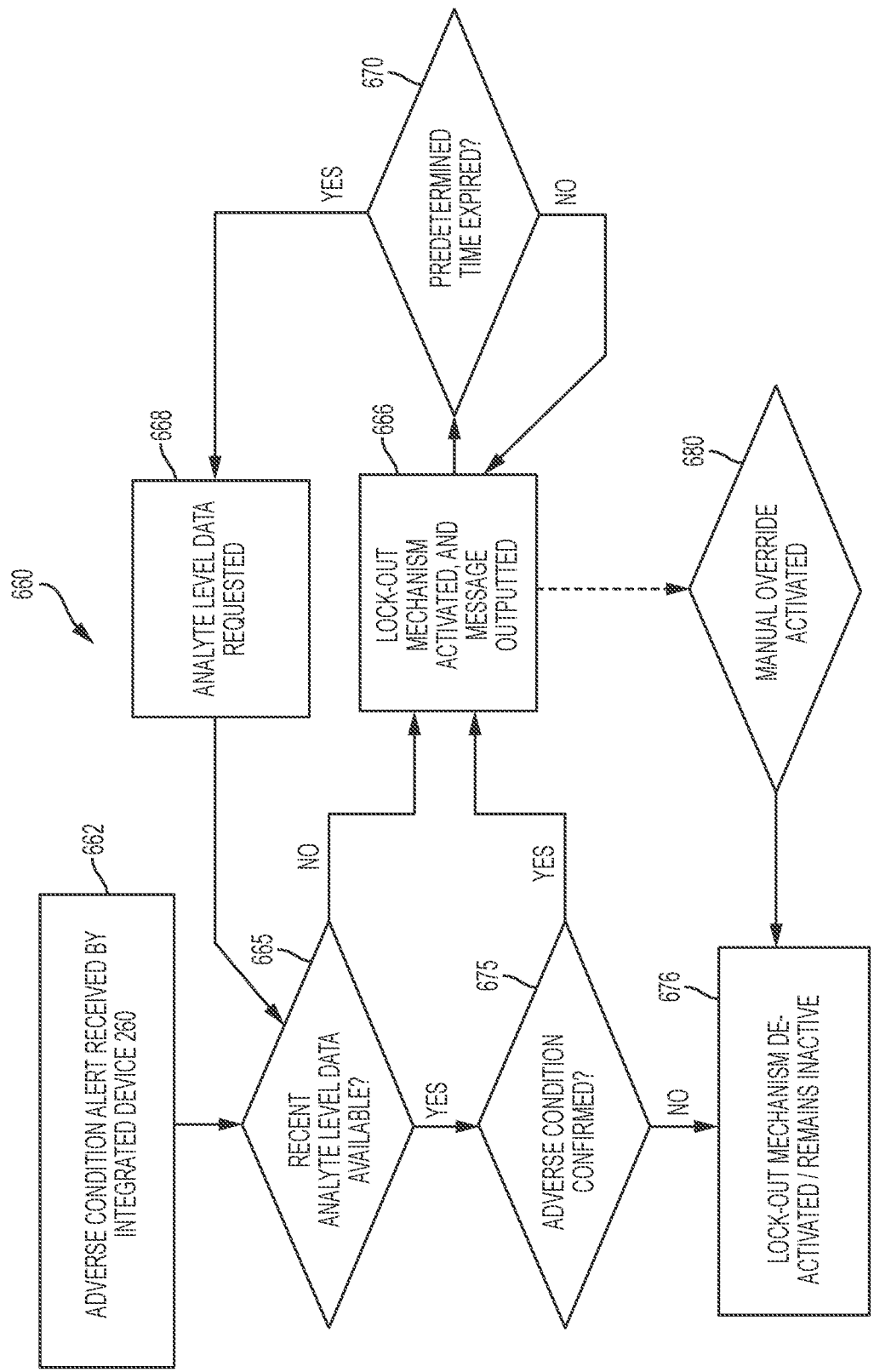

FIGS. 6C-6E are flowchart diagrams showing example methods for an adverse condition protection feature according to the embodiments disclosed herein. Before describing the steps, it should be understood that the adverse condition protection feature can include a feature to prevent the injection of insulin, or any other type of medication, by integrated device 260 in instances where there is an adverse condition, such as, for example, where there is a low glucose condition, medication already present in the subject, or an analyte level concentration that exceeds a predetermined threshold. Those of skill in the art will also recognize that any one or more of the methods or method steps described herein for preventing the injection of insulin, or any other type of medication, can be employed individually, or in combination with each other, and are within the scope of the present disclosure. In some embodiments, for example, an injection button can be inhibited such that it cannot be depressed. In an alternative embodiment, for example, a deadbolt latch, such as those described with respect to FIGS. 6A and 6B, can be activated. It will also be understood by those of skill in the art that, although the described methods and method steps, refer to the detection of an attempt to remove a cap as an initial step, the same methods and method steps can also be initiated by any set of predetermined actions (e.g., inserting medication into the medication reservoir, placing the integrated device 260 against a skin surface, etc.) that precede the injection of medication in the subject.

Referring to FIG. 6C, a flow diagram is provided of an example embodiment of a method 610 for an adverse condition protection feature. At Step 612, an adverse condition protection feature of integrated device 260 is activated when, for example, integrated device 260 receives an alert associated with an adverse condition from another device, such as sensor control device 102. In some embodiments, the adverse condition protection feature of integrated device 260 can be activated when integrated device 260 detects the removal of the cap (or an attempt by the subject to remove the cap), which can be sensed, for example, by an accelerometer in the cap. At Step 615, integrated device 260 determines if it has recent analyte level data either from sensor control device 102, or from another analyte measurement device with wireless communications capabilities, such as a glucose meter with a test strip port, or a reader device capable of relaying analyte level measurements from sensor control device 102. If recent analyte level data is not available then, at Step 616, a lock-out mechanism is activated, and a message is outputted to integrated device 260. In some embodiments, for example, the lock-out mechanism can include a deadbolt latch that is activated for a predetermined duration of time, as shown at Step 618, that can prevent the cap from being rotatably removed, as described with respect to FIGS. 6A and 6B. In other embodiments, the lock-out mechanism can inhibit the injection button from being depressed by the subject for the predetermined duration of time.

According to one aspect of the embodiments, the outputted message can include one or more of a visual, audio or vibratory output to integrated device 260. In some embodiments, for example, an indicator lamp or message can be displayed on device 260 to notify the subject to obtain an analyte level measurement, such as by performing a scan of sensor control device 102, taking a finger stick analyte level measurement, or manually entering an analyte level measurement through an input device. The outputted message can also include a visual display of a timer, showing a countdown of the predetermined time period, as shown at Step 618, during which the lock-out mechanism is activated.

According to another aspect of the embodiments, a manual override mechanism can be provided, such as a button or a switch on integrated device 260. At Step 625, if the manual override mechanism is activated by the subject, then the lock-out mechanism can be de-activated at Step 622. In some embodiments, the manual override mechanism can include a confirmation step, in which the subject is asked to enter a password through an input device, or in which the subject is asked to confirm activation of the manual override mechanism one or more times.

At Step 618, after the predetermined time has expired, method 610 returns to Step 615 to check if recent analyte level data is available. If recent analyte level data is still not available, method 610 repeats Steps 616 and 618, in which the lock-out mechanism is activated (or remains activated), and a message is outputted to integrated device 260.

Referring still to FIG. 6C, if recent analyte level data is available, then at Step 620, integrated device 260 can confirm whether an adverse condition is present in subject. In some embodiments, for example, instructions stored in memory 230 of integrated device 260, when executed by one or more processors 222 of integrated device 260, can cause processors 222 to perform the steps of comparing a recent analyte level measurement against a predetermined adverse condition threshold. If the absence of an adverse condition is confirmed, at step 622, no further action is taken (e.g., lock-out mechanism is de-activated or remains inactive), and integrated device 260 permits the medication delivery to occur. If an adverse condition is confirmed, at Step 616, the lock-out mechanism is activated, and a message is outputted to integrated device 260, as described above.

Referring to FIG. 6D, a flow diagram is provided of an example embodiment of a method 630 for a low glucose protection feature for integrated device 260. In many respects, method 630 includes several steps that are similar to the steps of example method 610, as described with respect to FIG. 6C. At Step 632, a low glucose protection feature is initiated when integrated device 260 detects an attempt to remove the cap, which can be sensed, for example, by an accelerometer in the cap. At Step 635, integrated device 260 determines if it has recent glucose level data either from sensor control device 102, or from another glucose measurement device with wireless communications capabilities. If recent glucose level data is not available, at Step 636, a lock-out mechanism (e.g., a deadbolt latch and/or an injection button inhibitor) is activated for a predetermined amount of time, and a message is outputted to integrated device 260. The outputted message can include a visual display of a timer, showing a countdown of the predetermined time period, as shown at Step 640, during which the lock-out mechanism is activated. In some embodiments, integrated device 260 can also include a manual override mechanism, as shown at Step 650, which can operate in a similar fashion to the manual override mechanism described with respect to FIG. 6C.

According to another aspect of the embodiments, after the predetermined duration of time has expired, at Step 640, recent glucose level data can be requested at Step 638. In some embodiments, the request for recent glucose level data can include displaying a message to the user to obtain a glucose level measurement, such as by performing a scan of sensor control device 102, taking a finger stick glucose level measurement, or manually entering an analyte level measurement through an input device. In other embodiments, the request for glucose level data can include transmitting a request for recent glucose level data to sensor control device 102, either with or without a notification to the subject.

Referring still to FIG. 6D, if recent glucose level data is available, then at Step 645, integrated device 260 can compare the recent glucose level data to a low glucose threshold (e.g., below 55 mg/dL). If the low glucose threshold is not exceeded, at Step 644, no further action is taken (e.g., lock-out mechanism is de-activated or remains inactive), and integrated device 260 permits the medication delivery to occur. If the low glucose threshold is exceeded, the lock-out mechanism is activated, and a message is outputted to integrated device 260, as described above with respect to Step 636. Moreover, although Step 645 of method 630 refers to a "low glucose threshold," those of skill in art will recognize that one or more other predetermined threshold values can be utilized, such as, for example, a glucose rate of change threshold, a rate of a rate of change, a glucose sensitivity threshold value, and the like.

Referring to FIG. 6E, a flow diagram is provided of an example embodiment of another method 660 for an adverse condition protection feature for integrated device 260. Like the previous embodiment, method 660 includes several steps that are similar to the steps of example method 610, as described with respect to FIG. 6C. In this embodiment, at Step 662, an adverse condition protection feature of integrated device 260 is activated when an adverse condition alert is received from another device, such as sensor control device 102. In some embodiments, for example, sensor control device 102 can transmit an alert to integrated device 260 according to a standard wireless communications protocol, such as, for example, a Bluetooth or Bluetooth Low Energy communications protocol, an NFC communications protocol, or an UHF communications protocol. According to one aspect of some embodiments, the transmission received by integrated device 260 can also include a recent analyte level measurement. In other embodiments, however, the transmission received by integrated device 260 can simply include an adverse condition alert without associated analyte level data.

At Step 665, integrated device 260 determines if it has recent analyte level data. If not, then at Step 666, a lock-out mechanism (e.g., a deadbolt latch and/or an injection button inhibitor) is activated for a predetermined duration of time, and a message is outputted to integrated device 260. In some embodiments, integrated device 260 can also include a manual override mechanism, as shown at Step 680, and as described above with respect to FIGS. 6C and 6D.

According to another aspect of the embodiments, after the predetermined time period has expired, at Step 670, recent analyte level data can be requested at Step 668. In some embodiments, the request for recent analyte level data can include displaying a message to the user to obtain an analyte level measurement, such as by performing a scan of sensor control device 102, taking a finger stick analyte level measurement, or manually entering an analyte level measurement through an input device. In other embodiments, the request for analyte level data can include transmitting a request for recent analyte level data to sensor control device 102, either with or without a notification to the subject.

Referring still to FIG. 6E, if recent analyte level data is available, then at Step 675, integrated device 260 can compare the recent analyte level data to an adverse condition threshold. If the adverse condition threshold is not exceeded, at Step 676, no further action is taken (e.g., lock-out mechanism is de-activated or remains inactive), and integrated device 260 can permit the medication delivery to occur. If the adverse condition threshold is exceeded, the lock-out mechanism is activated, and a message is outputted to integrated device 260, as described above with respect to Step 666.

Example Embodiments of Power Schemes for NFC Communications Circuitry

NFC protocols enable two communication devices to communicate over short distances. NFC devices can be categorized as either passive or active. Passive NFC devices can only send data and do not include a power source. Passive NFC devices are powered by the energy in the radio frequency (RF) field of a reader device. Active NFC devices can send or receive data and have their own power source.

Since active NFC devices have their own power source, the RF field from an active NFC device reader can be used to convey information. The distinction between passive and active NFC devices has an important impact on read range and on how much energy is needed in the RF field. For a reader, which is intended to operate at low power consumption levels, there is an advantage to reading from an active NFC device because less power is needed to be put into generating the RF field.

Referring back to FIG. 1, communication path 140 can use NFC communications protocols to communicate between integrated device 260 and sensor control device 102 when the devices are within a short range, typically less than a meter. NFC communication path 140 can use NFC protocols to employ electromagnetic induction between NFC enabled devices, sensor control device 102 and integrated device 260.

In order to perform the read operation, an NFC reader, e.g., integrated device 260, needs to generate a sufficient magnetic field to energize the circuitry in the device to be read, e.g., sensor control device 102. Since sensor control device 102 is a passive NFC device, integrated device 260 generates the current to provide the RF field capable of powering sensor control device 102. To achieve that magnetic field, a significant current flow is required in the loop antenna.

In prior art NFC readers, the NFC communication is done in one continuous operation with the antenna energized the entire time a message is sent and received. Maintaining this level of current can be challenging for small, battery operated devices, e.g., integrated device 260. However, the average current of this operation can be reduced by breaking up the communications into short bursts.

To generate the needed magnetic field intensity, a relatively high level of current is needed. Generating that high level of current for an extended period of time is challenging using a physically small battery. However, a number of battery chemistries are capable of supplying short bursts of high current at levels above their capacity, typically designated by the letter C. In an embodiment, this operation can be divided into multiple bursts that comply with the burst power capability of the chosen battery chemistry Referring back to FIG. 3A, in an embodiment, power supply 226 is a battery. Any type of battery capable of employing an electromagnetic induction to activate communication with sensor control device 102 can be implemented. However, due to the physical size of integrated device 260, a physically small battery can be used. Power supply 226 can be any chemistry battery, for example, lithium ion or lithium manganese batteries or a coin cell form factor can be used. Battery power supply 226 can provide a level of current according to the rating of the battery.

Communication circuitry 228 is powered by power supply 226. Communication circuitry 228 enables NFC communication path 140 with sensor control device 102. Communication circuitry 228 and power supply 226 provide current to antenna 229 sufficient to perform NFC communication with sensor control device 102.

In an embodiment, a user can initiate communication between integrated device 260 and the sensor control device 102 by using user interface 121. User interface 121 can be a button on the integrated device 260 or any other user interface to initiate communication path 140.

In an embodiment, integrated device 260 is in an inactive state and can be activated by a user action through the user interface 121. The user action can involve connecting the battery power supply 226 and activating integrated device 260, which includes power supply 226 generating a particular current threshold.

In an embodiment, an inductive recharging system (not shown) can be included in the integrated device 260 to recharge power supply 226.

Processor 222 can include one or more processors, microprocessors, controllers, and/or microcontrollers, each of which can be a discrete chip or distributed amongst (and a portion of) a number of different chips.

A non-transitory memory 230 is also included within integrated device 260 and can be shared by the various functional units present within integrated device 260, or can be distributed amongst two or more of them. Memory 230 can also be a separate chip. Memory 230 can be volatile and/or non-volatile memory.

In an embodiment, a current of 200 mA is required for communication between integrated device 260 and sensor control device 102. In an embodiment, power supply 226 is a battery that cannot produce the level of current required for continuous communication between sensor control device 102 and integrated device 260. In that embodiment (shown in FIG. 7), communication can be accomplished in short bursts rather than by continuous communication. In an embodiment, burst communication can be used until a response is received or the communication times out.

In an embodiment, memory 230 and processor 222 execute one or more instructions to break up a communication into short bursts. The short bursts can be determined based on the battery used on integrated device 260. In an embodiment, short bursts can be determined based on power demands or other configuration or design preferences of the system described. In an embodiment, a burst as short as 15 ms can be implemented with a spacing between bursts ranging between 30 ms and 45 ms. However, any burst length can be implemented such that the selected battery can support generating an appropriate current for the entire burst length and the burst length is shorter than the time required to send the entire transmission. Also, any time in between bursts can be implemented such that the battery can recover, and the delay is not detectable by a user enough to degrade the user experience. In an embodiment, communication bursts are implemented even though battery supply 226 in integrated device 260 is capable of maintaining the sufficient level of current for the entire length of the communication.

FIG. 7 is a system diagram depicting an example embodiment of a communication path between an integrated device and sensor control device. The communication path 140 in FIG. 1 is shown in FIG. 7. FIG. 7 shows communication between integrated device 260 and sensor control device 102 in bursts 741, 742, 743, 744, 745, and 746. Integrated device 260 can initiate communication with sensor control device 102 by employing a current sufficient to employ the appropriate magnetic field between integrated device 260 and sensor control device 102. In an embodiment, battery power supply 226 in integrated device 260 cannot maintain the sufficient level of current for the entire length of the communication. Therefore, the communication carrier signal can itself be sent in bursts such that the battery power supply 226 in integrated device 260 can provide the appropriate level of current. In an embodiment, communication bursts are implemented even though battery supply 226 in integrated device 260 is capable of maintaining the sufficient level of current for the entire length of the communication.

As shown in FIG. 7, integrated device 260 can communicate in a first burst 741, followed by a second burst 742 to an n burst 743. Furthermore, sensor control device 102 can also communicate in bursts using a first burst 744, followed by a second burst 745, to an n burst 746. In an embodiment using short bursts for communication, the current supplied can exceed the rating of the battery. In an embodiment, the current supplied can exceed the rating of the battery by two to three times.

Figure 8A:
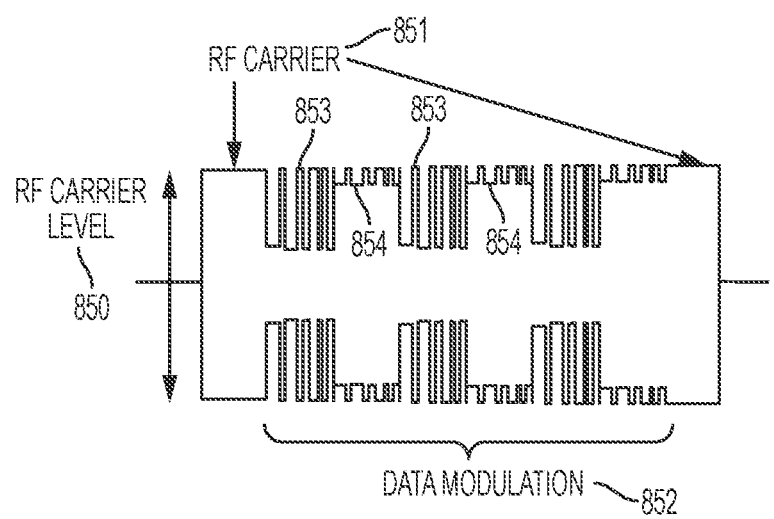
FIG. 8A is a data modulation diagram depicting an example from the prior art.
Figure 8B:
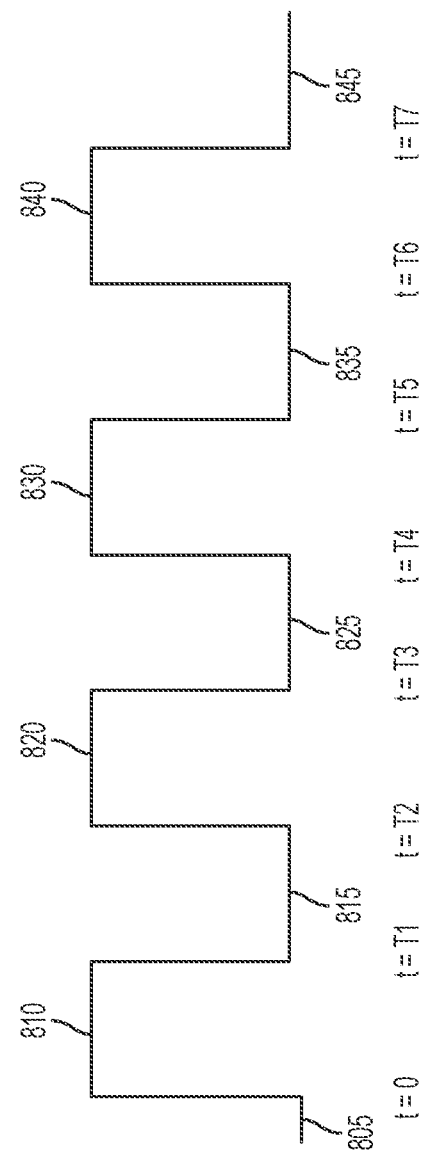
FIG. 8B is a timing diagram depicting an example embodiment of the timing of communication between an integrated device and a sensor control device.
Figure 8C:
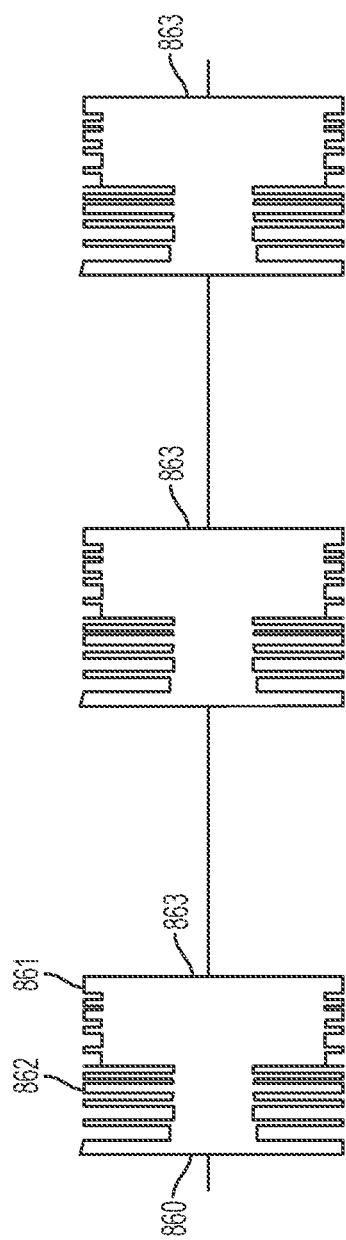
FIG. 8C is a data modulation diagram.

FIG. 8A is a data modulation diagram depicting an example from the prior art. FIG. 8B is a timing diagram depicting an example embodiment of the timing of communication between a pen and a sensor. FIG. 8C is a data modulation diagram depicting an example embodiment of the modulation used in NFC communication.

Since passive NFC devices rely on the power from an RF carrier to operate, most readers are designed to keep their RF carrier on during the entire read operation, including whatever time might be needed before and after communication for the NFC device to perform operations associated with the read operation, such as making a sensor measurement. However, in a small, battery powered device, like integrated device 260, keeping the RF carrier on for the entire read operation is challenging.

FIG. 8A depicts a modulation scheme from the prior art. FIG. 8A depicts data modulation 852 including an RF carrier level 850 and an RF carrier 851. Unmodulated RF carrier 851 can be any unmodulated RF carrier, for example, 13.56 MHz. Data modulation 853 represents an active NFC device sending a message to a passive NFC device. Data modulation 854 represents a response from a passive NFC device.

FIG. 8B is a timing diagram showing an example embodiment of the timing of communication between integrated device 260 and sensor control device 102. FIG. 8B shows no communication between integrated device 260 and sensor control device 102 at time t=0 shown by 805. At time t=0, communication begins, using pulses. Between time t=0 and t=T1 a communication burst occurs shown by 810. At time t=T1, the communication pulse ends and there is a break between pulses 815 until time t=T2. At time t=T2, the communication pulse switches on between time t=T2 and t=T3 as shown by 820. At time t=T3, the communication pulse switches off until time t=T4 as shown by 825. At time t=T4, the communication pulse switches on until time t=T5 as shown by 830. At time t=T5, the communication pulse switches off until time t=T6 as shown by 835. At time t=T6, the communication pulse switches on until time t=T7 as shown by 840. At time t=T7, communication pulse switches off as shown by 845.

In an embodiment, time T1 can be as small as 15 ms. Time T1 can also be greater than 15 ms. In an embodiment, time T2 can two or three times T1 or 45 to 60 ms, without degrading the user experience. In an embodiment, any T1 supported by the battery of integrated device 260 can be implemented. In an embodiment, any T2 can be implemented such that the delay is undetectable by the user.

As described above, the communication pulsing can occur until either a response is received or until a timeout occurs.

A typical NFC read operation as shown in FIG. 8A would last 150 to 300 ms. The bursts shown in FIGS. 8B and 8C can be as short as 15 ms each. The time between bursts can be extended out as far as necessary to lower the power consumption but limited by the time required to perform the complete read. If that time is too long, the user experience will be noticeably affected. An off to on ratio of two to three can be implemented without degrading the user experience.

FIG. 8C depicts a modulation scheme of an example embodiment. FIG. 8C depicts data modulation 862 including an RF carrier level 860 and an RF carrier 861. Further, FIG. 8C depicts a plurality of communication bursts 863. Each communication burst includes data modulation 862.

In an embodiment, communication bursts shown in FIGS. 8B and 8C can be employed. The communication bursts allow the average field strength, and thus the average reader power to support it, to be lower by the ratio of carrier on and off times. Lithium rechargeable batteries can supply higher peak current for short bursts than is possible for longer periods of time. Therefore, a smaller battery can be used when using communication bursts.

Figure 9:
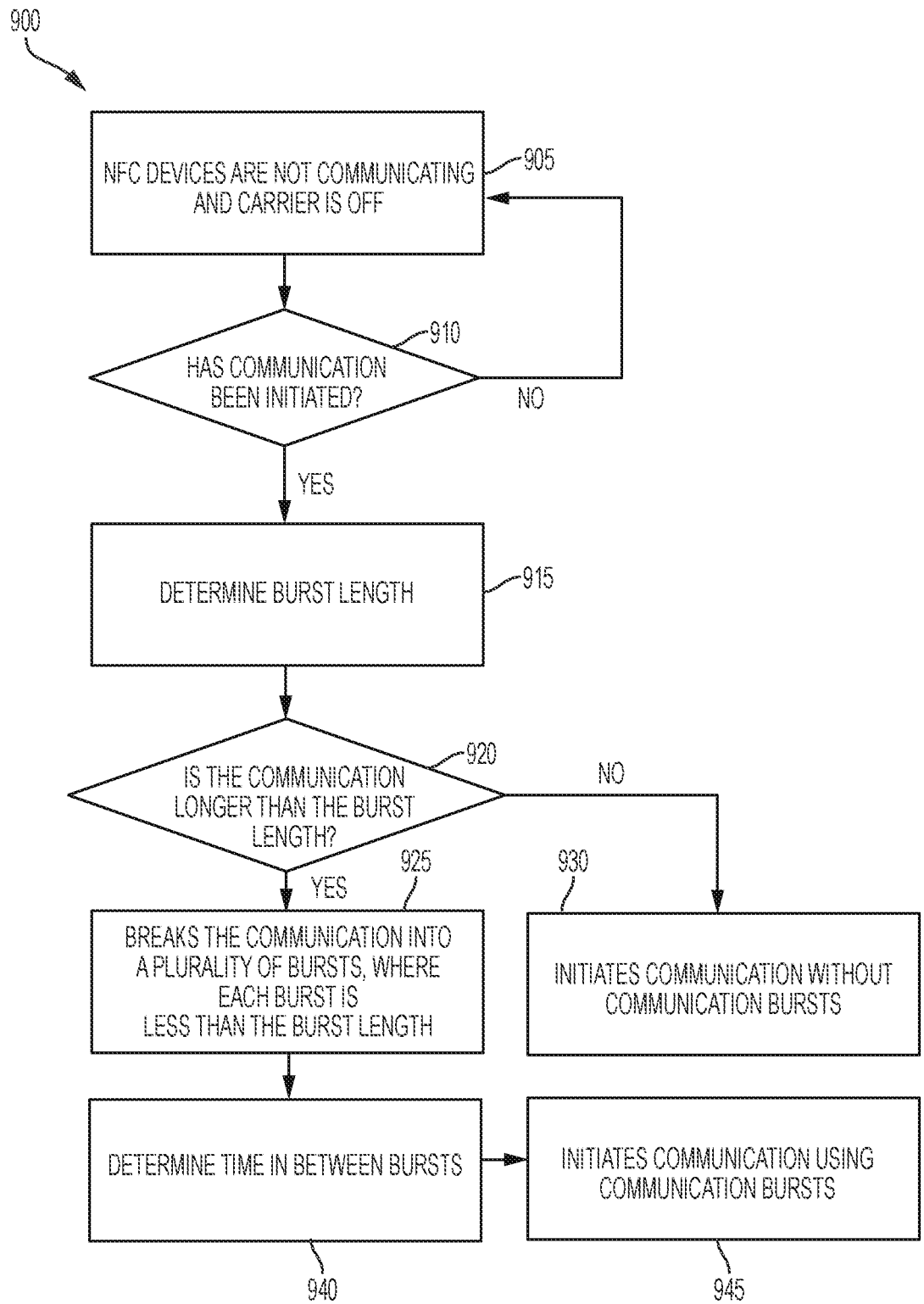
FIG. 9 is a flowchart depicting an example embodiment of the communication between an integrated device and a sensor control device.

FIG. 9 is a flowchart depicting an example embodiment of the communication between integrated device 260 and a sensor control device 102. FIG. 9 shows NFC devices are not communicating, and a carrier signal is off 905. An active NFC device checks to see if communication has been initiated 910. If communication has not been initiated 910, then NFC devices are not communicating, and carrier is off 905. If communication has been initiated 910, then determine the burst length 915. Communication can be initiated by a user pushing a button on the pen. In another embodiment, the communication can be initiated by another action by the user or another form of a user interfacing with the user interface.

Active NFC device checks if the communication is longer than the burst length 920. If the communication is not longer than the burst length 920, then active NFC device initiates communication without using bursts 930. If the communication is longer than the burst length 920, then the active NFC device breaks communication into a plurality of short bursts, where each burst is less than the burst length 925. Time in between bursts is also determined 940. FIG. 9 also shows initiating communication using the short bursts 945.

Figure 10:
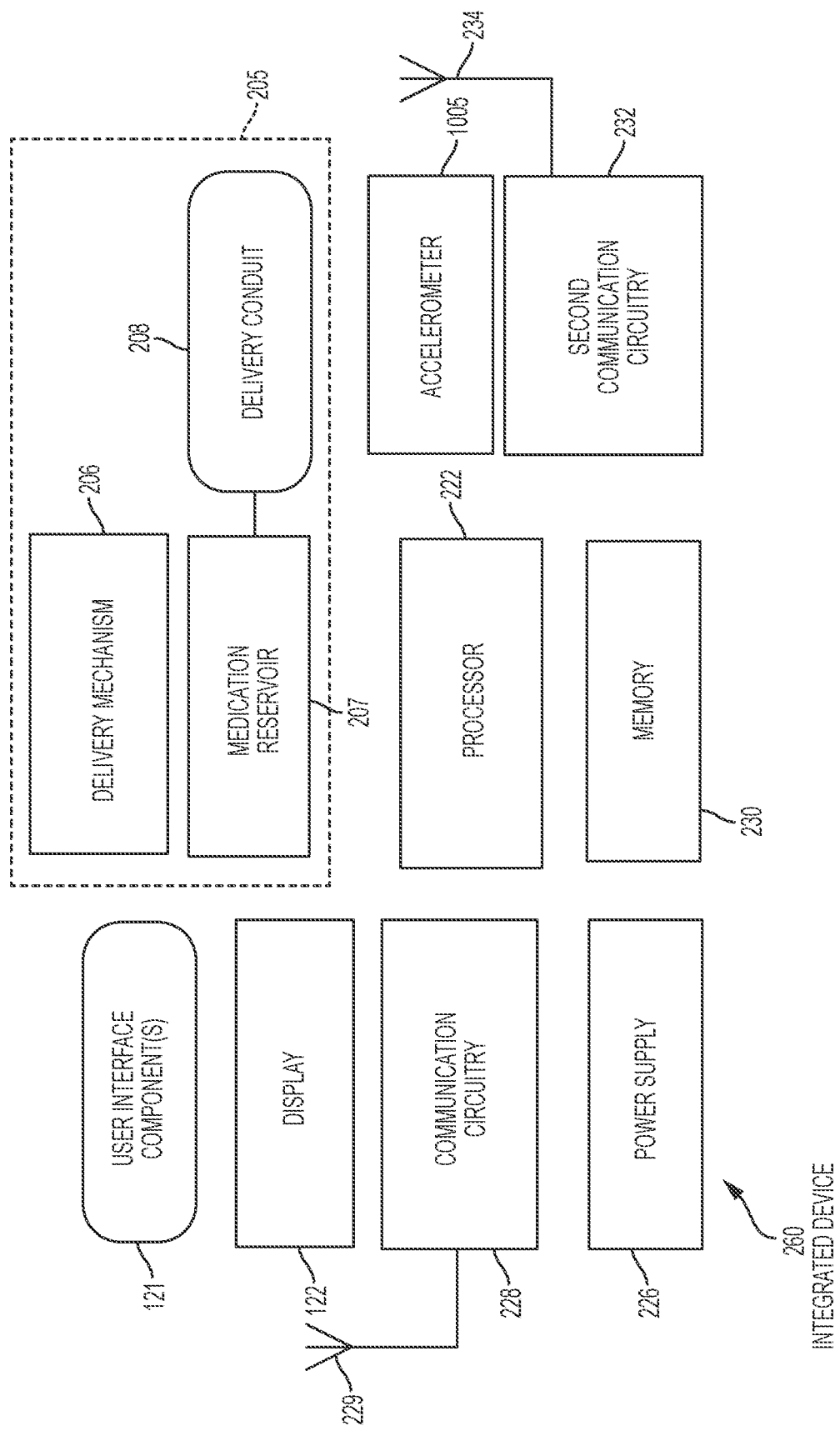
FIG. 10 is a block diagram depicting an example embodiment of an integrated device circuitry.

FIG. 10 is a block diagram depicting an example embodiment of an integrated device circuitry. FIG. 10 is similar to FIG. 3A with the addition of accelerometer 1005.

As described above, accelerometer 1005 can be coupled to the electronics, e.g., processor 222, memory 230, analog-to-digital converter, etc., within integrated device 260. Accelerometer 1005 can be configured to sense a "swiping" motion that is typical of the type of action a user would take to read a sensor control device 102 placed on his or her body (e.g., arm or abdomen). In this manner, in those embodiments that include an accelerometer 1005, integrated device 260 need not have a button or switch for activating the NFC scan function prior to scanning sensor control device 102 (or other device). Furthermore, because accelerometers consume relatively little power, i.e., typically less than a hundred microwatts, they can always be on and able to sense the swipe gesture yet consume significantly less power than a system driving the NFC antenna to scan for the sensor control device.

Figure 11:
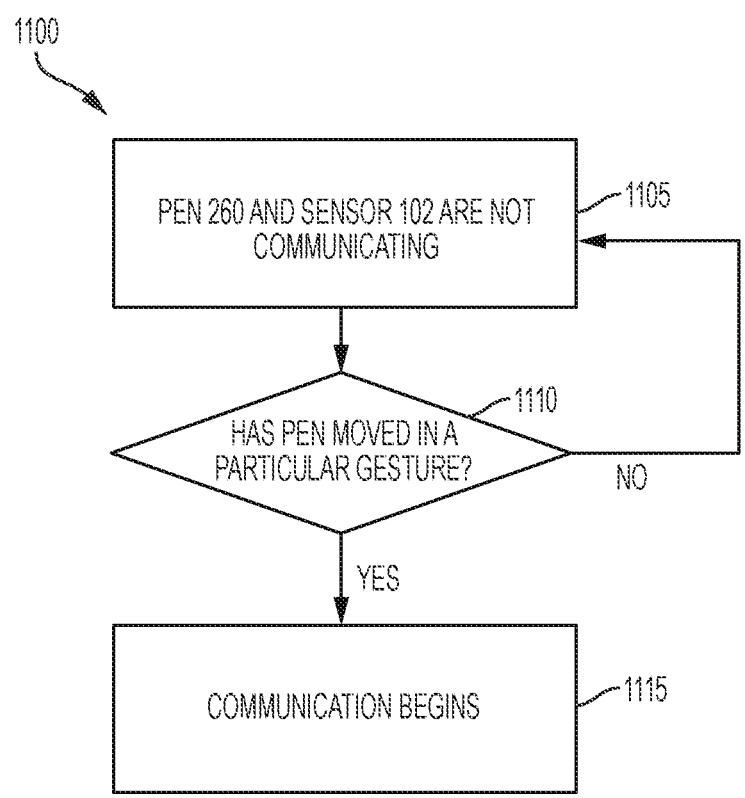
FIG. 11 is a flowchart depicting an example embodiment of an integrated device initiating communication with a sensor control device.

FIG. 11 is a flowchart depicting an example embodiment of a pen initiating communication with a sensor. Integrated device 260 and sensor control device 102 are not communicating 1105. Has the device moved in a particular gesture 1110. If yes, then communication begins 1115. If not, then integrated device 260 and sensor control device 102 are not communicating 1105.

The particular gesture can be any predetermined gesture that can be distinguished from typical motions associated with being carried, walked, or driven. For example, the particular gesture can be a swiping gesture, a wiggling gesture, a back and forth swiping gesture, or any other gesture.

Figure 12:
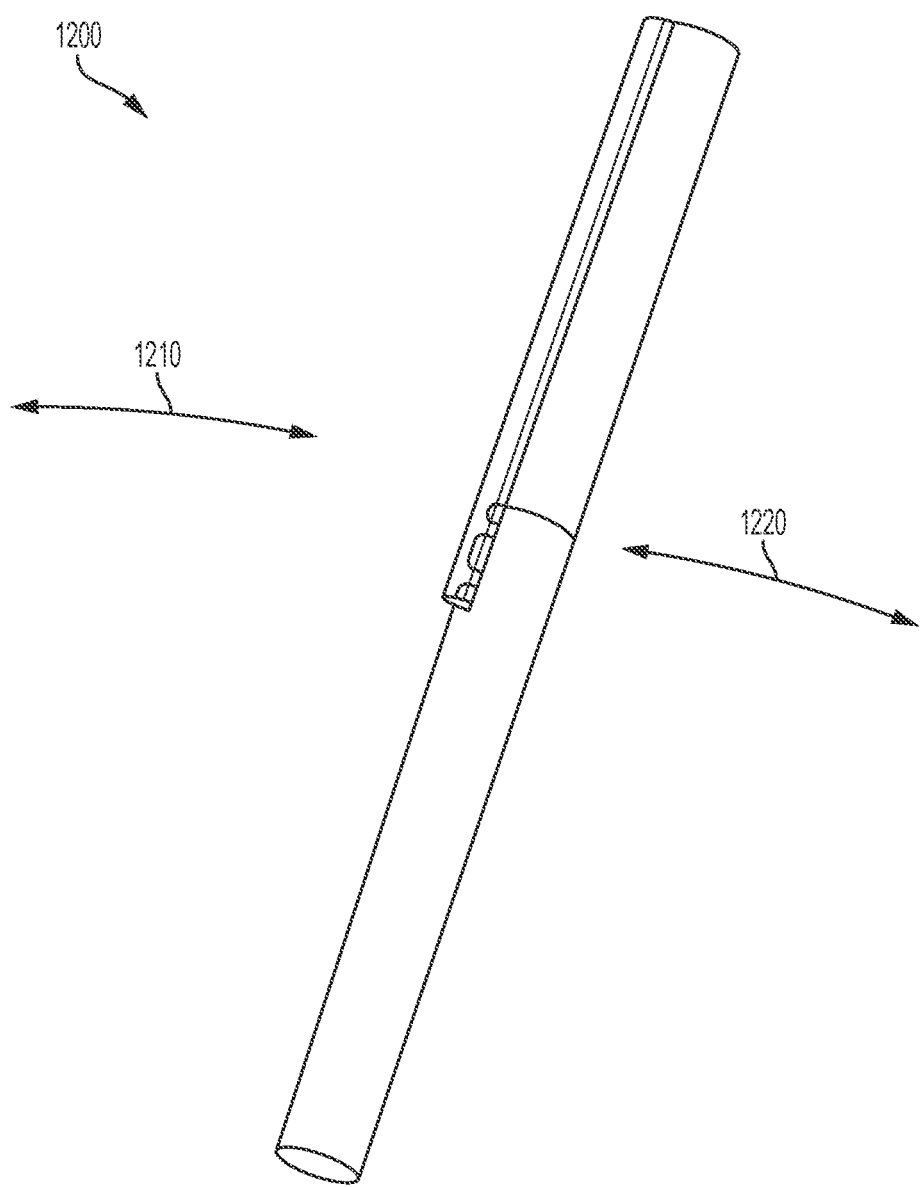
FIG. 12 is a diagram depicting an example embodiment gesture of a pen initiating communication with a sensor.

FIG. 12 is a diagram depicting an example embodiment gesture of a pen initiating communication with a sensor. FIG. 12 shows integrated device 260 moving back and forth 1210 and 1220 in a swiping motion. In an embodiment a single swipe from left to right or right can be used depending on the particular user and the location of sensor control device 102. In an embodiment, the gesture can be swipe back and forth, for example from left to right and from right to left. In an embodiment, the gesture can be wiggling type of gesture.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An integrated device enabled for communication with an electronics device, the integrated device comprising:
   a housing; and
   electronics contained within the housing, the electronics comprising:

a power supply capable of providing power to generate current pulses to provide a near field communication (NFC) communication with the electronics device;

a user interface coupled to the power supply enabled to permit initiation of the NFC communication with the electronics device;

an antenna providing the NFC communication with the electronics device in pulses each encoding data over a continuous interval;

one or more processors; and a memory coupled to the one or more processors, the memory including instructions that, when executed by the one or more processors, cause the one or more processors to:

determine whether to divide the NFC communication into the current pulses based on a total length of the NFC communication, and determine a length of each of the current pulses and a time in between the current pulses that divide the NFC communication into current pulses complying with a specified burst power capability of the power supply.

2. The device of claim 1, wherein the power supply is a battery.

3. The device of claim 2, wherein the battery is a lithium manganese battery.

4. The device of claim 2, wherein the battery is a lithium ion battery.

5. The device of claim 1, wherein the one or more processors implements a pulse length such that the power supply can provide adequate current during an entirety of the current pulse.

6. The device of claim 1, wherein the time between the current pulses is approximately twice the time as the length of each of the current pulses.

7. The device of claim 1, wherein each NFC communication is performed using a plurality of pulses.

8. The device of claim 1, wherein the one or more processors determine the pulse length and the time in between the current pulses such that the power supply can provide adequate current for the entirety of the NFC communication.

9. The device of claim 1, wherein the instructions, when executed by the one or more processors, further cause the one or more processors to cause transmission of the NFC communication without dividing the NFC communication into the current pulses if the total length of the NFC communication is not longer than the length of each of the current pulses.

10. A method of performing a near field (NFC) communication between an electronics device and an integrated device powered by a power supply, the method comprising:

receiving an initiation signal indicating initiation of the NFC communication;

initiating the NFC communication;

determining whether to divide the NFC communication into a plurality of communication pulses based on a total length of the NFC communication;

determining a pulse length for each communication pulse of the plurality of communication pulses such that the power supply can provide adequate current for an entirety of the each communication pulse;

determining a timing between a first communication pulse and a second communication pulse;

using the plurality of communication pulses complying with the pulse length and the timing to achieve the NFC communication, wherein the NFC communication occurs for the pulse length and ceases for the timing between the first pulse and the second pulse, iteratively until the NFC communication is complete.

11. The method of claim 10, wherein the NFC communication is accomplished using the plurality of communication pulses by generating a current for the pulse length and not generating a current for the timing between the first and second pulses.

12. The method of claim 11, wherein a battery generates the current.

13. The method of claim 12, wherein the battery is a lithium ion battery.

14. The method of claim 13, wherein the battery is a lithium manganese battery.

15. The method of claim 10, wherein the pulse length is greater than 15 milliseconds.

16. The method of claim 10, wherein the timing between the first and the second pulses is approximately twice the pulse length.

17. The method of claim 10, wherein determining the timing between the first pulse and the second pulse is performed such that the power supply can provide adequate current for an entirety of the NFC communication.

18. The method of claim 10, further comprising causing transmission of the NRC communication without dividing the NFC communication into a plurality of communication pulses if the total length of the NFC communication is not longer then the pulse length for each communication pulse of the plurality of communication pulses.

* * * * *